(12) United States Patent
Dunkel et al.

(10) Patent No.: US 7,728,019 B2
(45) Date of Patent: Jun. 1, 2010

(54) BIPHENYLCARBOXAMIDES

(75) Inventors: Ralf Dunkel, Monheim (DE); Hans-Ludwig Elbe, Wuppertal (DE); Heiko Rieck, Foy-lès-Lyon (FR); Ulrike Wachendorff-Neumann, Neuwied (DE); Peter Dahmen, Neuss (DE); Peter Lösel, Leverkusen (DE); Karl-Heinz Kuck, Langenfeld (DE); Astrid Mauler-Machnik, Leichlingen (DE); Jörg Nico Greul, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 739 days.

(21) Appl. No.: 10/538,242

(22) PCT Filed: Dec. 1, 2003

(86) PCT No.: PCT/EP03/13498

§ 371 (c)(1), (2), (4) Date: Mar. 23, 2007

(87) PCT Pub. No.: WO2004/054982

PCT Pub. Date: Jul. 1, 2004

(65) Prior Publication Data

US 2008/0085924 A1     Apr. 10, 2008

(30) Foreign Application Priority Data

Dec. 13, 2002    (DE) .................. 102 58 314

(51) Int. Cl.
| A01N 43/56 | (2006.01) |
| A01N 43/78 | (2006.01) |
| A01N 43/76 | (2006.01) |
| C07D 277/56 | (2006.01) |

(52) U.S. Cl. .................. 514/365; 514/406; 514/423; 548/200; 548/374.1; 548/537

(58) Field of Classification Search ........... None
See application file for complete search history.

(56) References Cited

U.S. PATENT DOCUMENTS

| 5,045,554 | A | 9/1991 | Alt et al. .................. 514/365 |
| 5,223,526 | A | 6/1993 | McLoughlin et al. ....... 514/406 |
| 5,330,995 | A | 7/1994 | Eicken et al. .............. 514/355 |
| 5,416,103 | A | 5/1995 | Eicken et al. .............. 514/355 |
| 5,438,070 | A | 8/1995 | Eicken et al. .............. 514/403 |
| 5,480,897 | A | 1/1996 | Eicken et al. .............. 514/365 |
| 5,556,988 | A | 9/1996 | Eicken et al. ............. 548/374.1 |
| 5,589,493 | A | 12/1996 | Eicken et al. .............. 514/355 |
| 5,922,732 | A | 7/1999 | Urch et al. .................. 514/304 |
| 5,968,947 | A | 10/1999 | Urch et al. .................. 514/299 |
| 6,093,726 | A | 7/2000 | Urch et al. .................. 514/299 |
| 6,147,104 | A | 11/2000 | Eicken et al. .............. 514/406 |
| 6,174,894 | B1 | 1/2001 | Urch et al. .................. 514/299 |
| 6,177,442 | B1 | 1/2001 | Urch et al. .................. 514/299 |
| 6,207,676 | B1 | 3/2001 | Urch et al. .................. 514/304 |
| 6,291,474 | B1 | 9/2001 | Brightwell et al. ......... 514/299 |
| 6,369,093 | B1 | 4/2002 | Elbe et al. .................. 514/406 |
| 6,391,883 | B1 | 5/2002 | Urch et al. .................. 514/255 |
| 6,573,275 | B1 | 6/2003 | Urch et al. .................. 514/304 |
| 7,176,228 | B2 * | 2/2007 | Elbe et al. .................. 514/406 |
| 2002/0061913 | A1 | 5/2002 | Urch et al. .................. 514/366 |

FOREIGN PATENT DOCUMENTS

| EP | 0 579 124 | 1/1994 |
| WO | 91/01311 | 2/1991 |
| WO | 02/08195 | 1/2002 |
| WO | 02/08197 | 1/2002 |

OTHER PUBLICATIONS

Synth. Commun., 30, (month unavailable) 2000, pp. 665-669, Pravin M Bendale and Bhushan M. Khadilkar, "Silica Gel Supported Chromium Trioxide: An Efficient Reagent for Oxidative Cleavage of Oximes to Carbonyl Compounds Under Mild Condition".
Synth. Commun., 29, (month unavailable) 1999, pp. 1697-1701, A.R. Hajipour et a., "Solid-Phase Synthesis of Oximes".

* cited by examiner

Primary Examiner—Kamal A Saeed
(74) Attorney, Agent, or Firm—Richard E. L. Henderson

(57) ABSTRACT

This invention relates to novel biphenylcarboxamides of the formula (I)

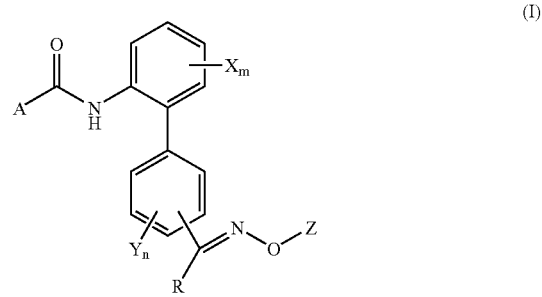

in which R, Z, X, Y, m, n and A are as defined in the disclosure, to a plurality of processes for preparing these compounds and their use for controlling unwanted microorganisms, and to novel intermediates and their preparation.

6 Claims, No Drawings

BIPHENYLCARBOXAMIDES

The present patent application has been filed under 35 U.S.C. 371 as a national stage application of PCT/EP2003/013498, filed Dec. 1, 2003, which was published in German as International Patent Publication WO 2004/054982 on Jul. 1, 2004, and is entitled to the right of priority of German Patent Application 102 58 314.5, filed Dec. 13, 2002.

The present invention relates to novel biphenylcarboxamides, to a plurality of processes for their preparation and to their use for controlling unwanted microorganisms.

It is already known that numerous carboxanilides have fungicidal properties (compare WO 93/11 117, WO 99/09 013, WO 00/14 071, EP-A 0 545 099 and EP-A 0 589 301). In particular, WO 02/08195 and WO 02/08197 disclose oxyiminomethyl-substituted carboxamides. The activity of these compounds is good; however, it is sometimes unsatisfactory.

This invention now provides novel biphenylcarboxamides of the formula (I)

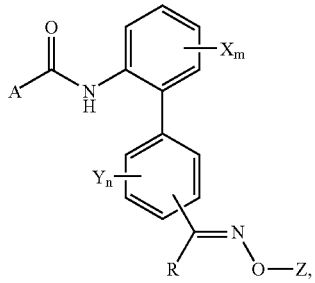

(I)

in which
R represents hydrogen, $C_1$-$C_6$-alkyl or $C_1$-$C_3$-haloalkyl having in each case 1 to 7 fluorine, chlorine and/or bromine atoms,
Z represents $C_3$-$C_8$-alkenyl, $C_3$-$C_8$-alkynyl, $C_3$-$C_8$-haloalkenyl, $C_3$-$C_8$-haloalkynyl having in each case 1 to 5 fluorine, chlorine and/or bromine atoms, or ($C_3$-$C_8$-cycloalkyl)($C_1$-$C_4$-alkyl),
X and Y independently of one another represent halogen, cyano, nitro, $C_1$-$C_8$-alkyl, $C_1$-$C_8$-alkoxy, $C_1$-$C_8$-alkylthio, $C_1$-$C_6$-haloalkyl, $C_1$-$C_6$-haloalkoxy or $C_1$-$C_6$-haloalkylthio having in each case 1 to 13 fluorine, chlorine and/or bromine atoms,
m represents 0, 1, 2, 3 or 4, where x represents identical or different radicals if m represents 2, 3 or 4,
n represents 0, 1, 2, 3 or 4, where y represents identical or different radicals if n represents 2, 3 or 4,
and
A represents a radical of the formula

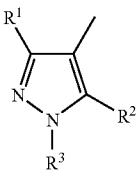

in which
$R^1$ represents hydrogen, cyano, halogen, nitro, $C_1$-$C_4$-alkyl, $C_3$-$C_6$-cycloalkyl, $C_1$-$C_4$-alkoxy, $C_1$-$C_4$-alkylthio, aminocarbonyl, aminocarbonyl-$C_1$-$C_4$-alkyl or represents $C_1$-$C_4$-haloalkyl, $C_1$-$C_4$-haloalkoxy, $C_1$-$C_4$-haloalkylthio having in each case 1 to 5 halogen atoms, and
$R^2$ represents hydrogen, halogen, cyano, $C_1$-$C_4$-alkyl, $C_1$-$C_4$-alkoxy or $C_1$-$C_4$-alkylthio and
$R^3$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, or represents $C_1$-$C_4$-haloalkyl, halo($C_1$-$C_4$-alkylthio-$C_1$-$C_4$-alkyl), halo($C_1$-$C_4$-alkoxy-$C_1$-$C_4$-alkyl) having in each case 1 to 5 halogen atoms or represents phenyl, or
A represents a radical of the formula

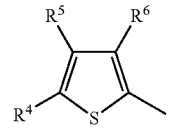

in which
$R^4$ and $R^5$ independently of one another represent hydrogen, halogen, $C_1$-$C_4$-alkyl or $C_1$-$C_4$-haloalkyl having 1 to 5 halogen atoms and
$R^6$ represents halogen, cyano or $C_1$-$C_4$-alkyl, $C_1$-$C_4$-haloalkyl, $C_1$-$C_4$-haloalkoxy having in each case 1 to 5 halogen atoms, or
A represents a radical of the formula

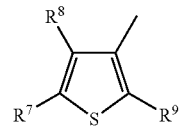

in which
$R^7$ and $R^8$ independently of one another represent hydrogen, halogen, $C_1$-$C_4$-alkyl or $C_1$-$C_4$-haloalkyl having 1 to 5 halogen atoms and
$R^9$ represents hydrogen, halogen or $C_1$-$C_4$-alkyl, or
A represents a radical of the formula

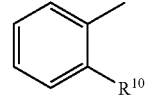

in which
$R^{10}$ represents hydrogen, halogen, hydroxyl, cyano, $C_1$-$C_6$-alkyl, $C_1$-$C_4$-haloalkyl, $C_1$-$C_4$-haloalkoxy, $C_1$-$C_4$-haloalkylthio having in each case 1 to 5 halogen atoms, or
A represents a radical of the formula

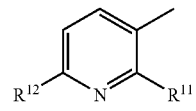

in which
$R^{11}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, $C_1$-$C_4$-haloalkylthio having in each case 1 to 5 halogen atoms and
$R^{12}$ represents hydrogen, halogen, cyano, $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl or represents $C_1$-$C_4$-haloalkyl, $C_1$-$C_4$-haloalkoxy having in each case 1 to 5 halogen atoms, or A represents a radical of the formula

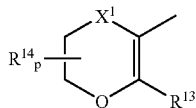

in which
$R^{13}$ represents $C_1$-$C_4$-alkyl or represents $C_1$-$C_4$-haloalkyl having 1 to 5 halogen atoms,
$R^{14}$ represents $C_1$-$C_4$-alkyl,
$X^1$ represents S (sulfur), represents SO, $SO_2$ or $CH_2$ and
p represents 0, 1 or 2, or A represents a radical of the formula

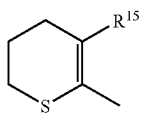

in which
$R^{15}$ represents $C_1$-$C_4$-alkyl or represents $C_1$-$C_4$-haloalkyl having 1 to 5 halogen atoms, or A represents a radical of the formula

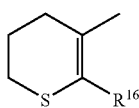

in which
$R^{16}$ represents $C_1$-$C_4$-alkyl or represents $C_1$-$C_4$-haloalkyl having 1 to 5 halogen atoms, or A represents a radical of the formula

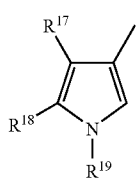

in which
$R^{17}$ represents halogen, cyano, $C_1$-$C_4$-alkyl or represents $C_1$-$C_4$-haloalkyl having 1 to 5 halogen atoms,
$R^{18}$ represents hydrogen, halogen, $C_1$-$C_4$-alkyl or represents $C_1$-$C_4$-haloalkyl having 1 to 5 halogen atoms,
$R^{19}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkysulfonyl, di($C_1$-$C_4$-alkyl)aminosulfonyl, $C_1$-$C_6$-alkylcarbonyl or represents optionally substituted phenylsulfonyl or benzoyl, or A represents a radical of the formula

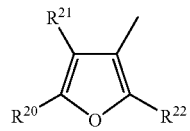

in which
$R^{20}$ and $R^{21}$ independently of one another represent hydrogen, halogen, amino, $C_1$-$C_4$-alkyl or represent $C_1$-$C_4$-haloalkyl having 1 to 5 halogen atoms and
$R^{22}$ represents hydrogen, halogen, $C_1$-$C_4$-alkyl or represents $C_1$-$C_4$-haloalkyl having 1 to 5 halogen atoms, or A represents a radical of the formula

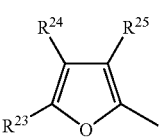

in which
$R^{23}$ and $R^{24}$ independently of one another represent hydrogen, halogen, amino, nitro, $C_1$-$C_4$-alkyl or represent $C_1$-$C_4$-haloalkyl having 1 to 5 halogen atoms and
$R^{25}$ represents hydrogen, halogen, $C_1$-$C_4$-alkyl or represents $C_1$-$C_4$-haloalkyl having 1 to 5 halogen atoms, or A represents a radical of the formula

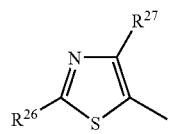

in which
$R^{26}$ represents hydrogen, halogen, amino, $C_1$-$C_4$-alkylamino, di-($C_1$-$C_4$-alkyl)amino, cyano, $C_1$-$C_4$-alkyl or represents $C_1$-$C_4$-haloalkyl having 1 to 5 halogen atoms and
$R^{27}$ represents halogen, $C_1$-$C_4$-alkyl or $C_1$-$C_4$-haloalkyl having 1 to 5 halogen atoms, or A represents a radical of the formula

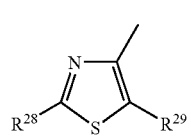

in which
R²⁸ represents hydrogen, halogen, amino, $C_1$-$C_4$-alkylamino, di-$C_1$-$C_4$-alkyl)amino, cyano, $C_1$-$C_4$-alkyl or represents $C_1$-$C_4$-haloalkyl having 1 to 5 halogen atoms and
R²⁹ represents halogen, $C_1$-$C_4$-alkyl or $C_1$-$C_4$-haloalkyl having 1 to 5 halogen atoms, or
A represents a radical of the formula

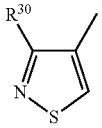

in which
R³⁰ represents halogen, $C_1$-$C_4$-alkyl, $C_1$-$C_4$-haloalkyl having 1 to 5 halogen atoms, or
A represents a radical of the formula

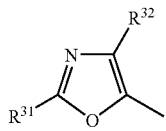

in which
R³¹ represents hydrogen or $C_1$-$C_4$-alkyl and
R³² represents halogen or $C_1$-$C_4$-alkyl, or
A represents a radical of the formula

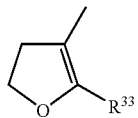

in which
R³³ represents $C_1$-$C_4$-alkyl or $C_1$-$C_4$-haloalkyl having 1 to 5 halogen atoms, or
A represents a radical of the formula

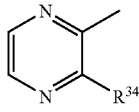

in which
R³⁴ represents hydrogen, halogen, $C_1$-$C_4$-alkyl or $C_1$-$C_2$-haloalkyl having 1 to 5 halogen atoms.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and the threo and erythro-, and also the optical isomers, any mixtures of these isomers, and also the possible tautomeric forms.

In particular with reference to the oxime double bond, E/Z isomers occur when R is $C_1$-$C_6$-alkyl. These isomers are generally present as a mixture. The configuration given below in structural formulae always includes both possibilities. For the sake of simplicity, only one isomer is shown in each case.

Furthermore, it has been found that biphenylcarboxamides of the formula (I) are obtained when a) carboxylic acid derivatives of the formula (II)

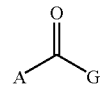
(II)

in which
A is as defined above and
G represents halogen, hydroxyl or $C_1$-$C_6$-alkoxy are reacted with aniline derivatives of the formula (III)

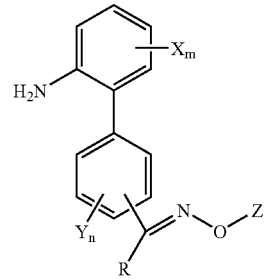
(III)

in which
R, Z, X, Y, m and n are as defined above,
if appropriate in the presence of a catalyst, if appropriate in the presence of an acid binder and if appropriate in the presence of a diluent, or
b) carboxamide derivatives of the formula (IV)

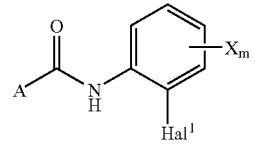
(IV)

in which
A, X and m are as defined above,
Hal¹ represents bromine or iodine,
are reacted with boronic acid derivatives of the formula (V)

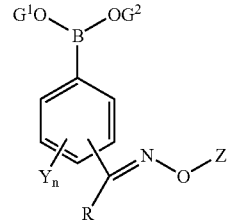
(V)

in which
R, Z, Y and n are as defined above and
G¹ and G² each represent hydrogen or together represent tetramethylethylene in the presence of a catalyst, if appropriate in the presence of an acid binder and if appropriate in the presence of a diluent, or c) carboxamide boronic acid derivatives of the formula (VI)

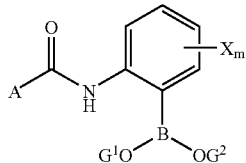

(VI)

in which
A, X and m are as defined above and
G¹ and G² each represent hydrogen or together represent tetramethylethylene are reacted with phenyl oxime derivatives of the formula (VII)

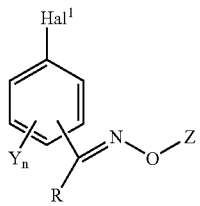

(VII)

in which
R, Z, Y and n are as defined above,
Hal¹ represents bromine or iodine,
in the presence of a catalyst, if appropriate in the presence of an acid binder and if appropriate in the presence of a diluent, or d) biphenylacyl derivatives of the formula (VII)

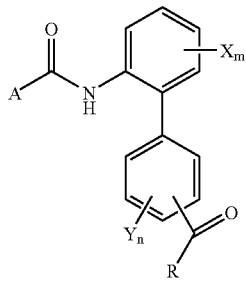

(VIII)

in which
A, R, X, Y, m and n are as defined above,
are reacted with hydroxylamine derivatives of the formula (IX)

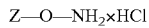  Z—O—NH$_2$×HCl     (IX)

in which
Z is as defined above,
if appropriate in the presence of an acid binder and if appropriate in the presence of a diluent, or e) hydroxyimino derivatives of the formula (I-a)

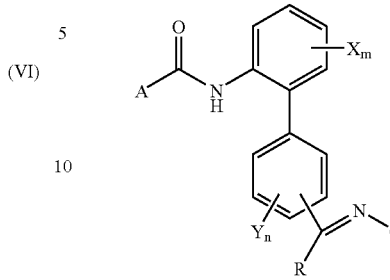

(I-a)

in which
A, R, X, Y, m and n are as defined above
are reacted with compounds of the formula (X)

Z-E     (X)

in which
Z is as defined above,
E represents chlorine, bromine, iodine, methanesulfonyl or p-toluenesulfonyl,
if appropriate in the presence of an acid binder and if appropriate in the presence of a diluent, or f) carboxamide derivatives of the formula (IV)

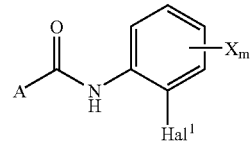

(IV)

in which
A, X and m are as defined above,
Hal¹ represents bromine or iodine,
are reacted with phenyl oxime derivatives of the formula (VII)

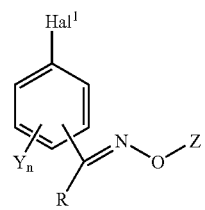

(VII)

in which
R, Z, Y and n are as defined above,
Hal¹ represents bromine or iodine
in the presence of a palladium or platinum catalyst and in the presence of 4,4,4',4',5,5,5',5'-octamethyl-2,2'-bis-1,3,2-dioxaborolane, if appropriate in the presence of an acid binder and if appropriate in the presence of a diluent.

Finally, it has been found that novel biphenylcarboxamides of the formula (I) have very good microbicidal properties and can be used for controlling unwanted microorganisms both in crop protection and in the protection of materials.

Surprisingly, the biphenylcarboxmides of the formula (I) according to the invention have considerably better fungicidal activity than the constitutionally most similar active compounds of the prior art having the same direction of action.

The formula (I) provides a general definition of the biphenylcarboxamides according to the invention.

R preferably represents hydrogen, $C_{1-4}$-alkyl or $C_1$-$C_3$-haloalkyl having in each case 1 to 7 fluorine, chlorine and/or bromine atoms.

Z preferably represents $C_3$-$C_6$-alkenyl, $C_3$-$C_6$-alkynyl, $C_3$-$C_6$-haloalkenyl, $C_3$-$C_6$-haloalkynyl having in each case 1 to 5 fluorine, chlorine and/or bromine atoms, or ($C_3$-$C_6$-cycloalkyl)-($C_1$-$C_4$-alkyl).

X and Y independently of one another preferably represent fluorine, chlorine, bromine, cyano, nitro, $C_1$-$C_6$-alkyl, $C_1$-$C_6$-alkoxy, $C_1$-$C_6$-alkylthio, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

m preferably represents 0, 1, 2 or 3, where x represents identical or different radicals if m represents 2 or 3.

n preferably represents 0, 1, 2 or 3, where y represents identical or different radicals if n represents 2 or 3.

A preferably represents a radical of the formula

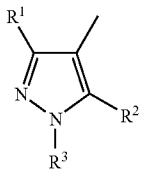

in which $R^1$ represents hydrogen, cyano, fluorine, chlorine, bromine, iodine, methyl, ethyl, isopropyl, cyclopropyl, methoxy, ethoxy, methylthio, ethylthio, aminocarbonyl, aminocarbonylmethyl, aminocarbonylethyl, $C_1$-$C_2$-haloalkyl $C_1$-$C_2$-haloalkoxy having in each case 1 to 5 fluorine, chlorine and/or bromine atoms, trifluoromethylthio or difluoromethylthio, $R^2$ represents hydrogen, fluorine, chlorine, bromine, iodine, methyl, ethyl, methoxy, ethoxy, methylthio or ethylthio and $R^3$ represents hydrogen, methyl, ethyl, n-propyl, isopropyl, hydroxymethyl, hydroxyethyl, cyclopropyl, cyclopentyl, cyclohexyl, $C_1$-$C_2$-haloalkyl having 1 to 5 fluorine, chlorine and/or bromine atoms or represents phenyl.

A furthermore preferably represents a radical of the formula

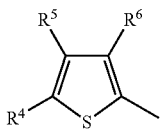

in which $R^4$ and $R^5$ independently of one another represent hydrogen, fluorine, chlorine, bromine, methyl, ethyl or $C_1$-$C_2$-haloalkyl having 1 to 5 fluorine, chlorine and/or bromine atoms and $R^6$ represents fluorine, chlorine, bromine, iodine, cyano, methyl, ethyl, trifluoromethyl or $C_1$-$C_2$-haloalkoxy having 1 to 5 fluorine, chlorine and/or bromine atoms.

A furthermore preferably represents a radical of the formula

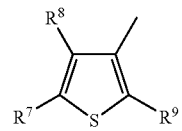

in which $R^7$ and $R^8$ independently of one another represent hydrogen, fluorine, chlorine, bromine, methyl, ethyl or $C_1$-$C_2$-haloalkyl having 1 to 5 fluorine, chlorine and/or bromine atoms and $R^9$ represents hydrogen, fluorine, chlorine, bromine, methyl or ethyl.

A furthermore preferably represents a radical of the formula

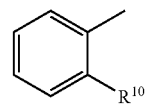

in which $R^{10}$ represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy, $C_1$-$C_2$-haloalkylthio having in each case 1 to 5 fluorine, chlorine and/or bromine atoms.

A furthermore preferably represents a radical of the formula

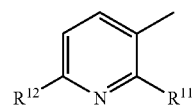

in which $R^{11}$ represents fluorine, chlorine, bromine, iodine, hydroxyl, cyano, $C_1$-$C_4$-alkyl, methoxy, ethoxy, methylthio, ethylthio, $C_1$-$C_2$-haloalkyl, $C_1$-$C_2$-haloalkoxy having in each case 1 to 5 fluorine, chlorine and/or bromine atoms, trifluoromethylthio, difluoromethylthio and $R^{12}$ represents hydrogen, fluorine, chlorine, bromine, iodine, cyano, $C_1$-$C_4$-alkyl, methoxy, ethoxy, methylthio, ethylthio, $C_1$-$C_2$-alkylsulfinyl, $C_1$-$C_2$-alkylsulfonyl, $C_1$-$C_2$-haloalkyl, $C_1$-$C_2$-haloalkoxy having in each case 1 to 5 fluorine, chlorine and/or bromine atoms.

A furthermore preferably represents a radical of the formula

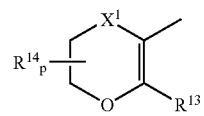

in which $R^{13}$ represents methyl, ethyl or represents $C_1$-$C_2$-haloalkyl having 1 to 5 fluorine, chlorine and/or bromine atoms and $R^{14}$ represents methyl or ethyl, $X^1$ represents S (sulfur), represents SO, $SO_2$ or $CH_2$ and p represents 0, 1 or 2.

A furthermore preferably represents a radical of the formula

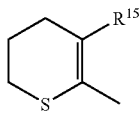

in which
R¹⁵ represents methyl, ethyl or represents $C_1$-$C_2$-haloalkyl having 1 to 5 fluorine, chlorine and/or bromine atoms.

A furthermore preferably represents a radical of the formula

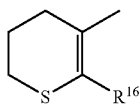

in which
R¹⁶ represents methyl, ethyl or represents $C_1$-$C_2$-haloalkyl having 1 to 5 fluorine, chlorine and/or bromine atoms.

A furthermore preferably represents a radical of the formula

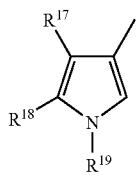

in which
R¹⁷ represents fluorine, chlorine, bromine, cyano, methyl, ethyl, isopropyl or represents $C_1$-$C_2$-haloalkyl having 1 to 5 fluorine, chlorine and/or bromine atoms,
R¹⁸ represents hydrogen, fluorine, chlorine, bromine, methyl, ethyl or represents $C_1$-$C_2$-haloalkyl having 1 to 5 fluorine, chlorine and/or bromine atoms and
R¹⁹ represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulfonyl or dimethylaminosulfonyl.

A furthermore preferably represents a radical of the formula

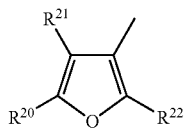

in which
R²⁰ and R²¹ independently of one another represent hydrogen, fluorine, chlorine, bromine, amino, methyl, ethyl or represents $C_1$-$C_2$-haloalkyl having 1 to 5 fluorine, chlorine and/or bromine atoms and
R²² represents hydrogen, fluorine, chlorine, bromine, methyl, ethyl or represents $C_1$-$C_2$-haloalkyl having 1 to 5 fluorine, chlorine and/or bromine atoms.

A furthermore preferably represents a radical of the formula

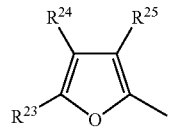

in which
R²³ and R²⁴ independently of one another represent hydrogen, fluorine, chlorine, bromine, amino, nitro, methyl, ethyl or represent $C_1$-$C_2$-haloalkyl having 1 to 5 fluorine, chlorine and/or bromine atoms and
R²⁵ represents hydrogen, fluorine, chlorine, bromine, methyl, ethyl or represents $C_1$-$C_2$-haloalkyl having 1 to 5 fluorine, chlorine and/or bromine atoms.

A furthermore preferably represents a radical of the formula

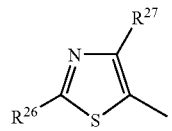

in which
R²⁶ represents hydrogen, fluorine, chlorine, bromine, amino, $C_1$-$C_4$-alkylamino, di($C_1$-$C_4$-alkyl)amino, cyano, methyl, ethyl or represents $C_1$-$C_2$-haloalkyl having 1 to 5 fluorine, chlorine and/or bromine atoms and
R²⁷ represents fluorine, chlorine, bromine, methyl, ethyl or $C_1$-$C_2$-haloalkyl having 1 to 5 fluorine, chlorine and/or bromine atoms.

A furthermore preferably represents a radical of the formula

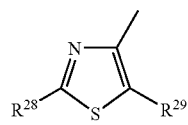

in which
R²⁸ represents hydrogen, fluorine, chlorine, bromine, amino, $C_1$-$C_4$-alkylamino, di-($C_1$-$C_4$-alkyl)amino, cyano, methyl, ethyl or represents $C_1$-$C_2$-haloalkyl having 1 to 5 fluorine, chlorine and/or bromine atoms and
R²⁹ represents fluorine, chlorine, bromine, methyl, ethyl or $C_1$-$C_2$-haloalkyl having 1 to 5 fluorine, chlorine and/or bromine atoms.

A furthermore preferably represents a radical of the formula

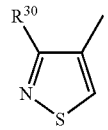

in which
R³⁰ represents fluorine, chlorine, bromine, methyl, ethyl or $C_1$-$C_2$-haloalkyl having 1 to 5 fluorine, chlorine and/or bromine atoms.

A furthermore preferably represents a radical of the formula

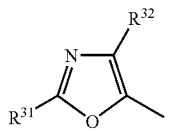

in which
R$^{31}$ represents hydrogen, methyl or ethyl and
R$^{32}$ represents fluorine, chlorine, bromine, methyl or ethyl.

A furthermore preferably represents a radical of the formula

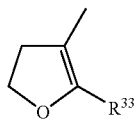

in which
R$^{33}$ represents methyl, ethyl or C$_1$-C$_2$-haloalkyl having 1 to 5 fluorine, chlorine and/or bromine atoms.

A furthermore preferably represents a radical of the formula

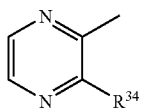

in which
R$^{34}$ represents hydrogen, fluorine, chlorine, bromine, methyl, ethyl or trifluoromethyl.

R particularly preferably represents hydrogen, methyl, ethyl, isopropyl, tert-butyl.

Z particularly preferably represents allyl, 2-butenyl, 2-methylallyl, 1-methylallyl, 3-methyl-2-butenyl, propargyl, 2-butynyl, 3-butynyl, 2-methyl-3-butynyl, 3,3-difluoroallyl, 3,3-dichloroallyl, cyclopropylmethyl, cyclopentylmethyl, cyclohexylmethyl.

X and Y independently of one another particularly preferably represent fluorine, chlorine, bromine, cyano, nitro, methyl, ethyl, n-propyl, isopropyl, n-butyl, sec-butyl, isobutyl, tert-butyl, methoxy, ethoxy, methylthio, trichloromethyl, trifluoromethyl, difluoromethyl, difluorochloromethyl, difluoromethoxy, trifluoromethoxy, trifluoromethylthio, difluorochloromethylthio, m particularly preferably represents 0 or 1.

n particularly preferably represents 0, 1 or 2, where y represents identical or different radicals if n represents 2.

A particularly preferably represents a radical of the formula

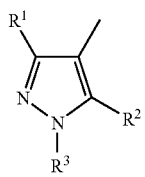

in which
R$^1$ represents hydrogen, fluorine, chlorine, bromine, iodine, methyl, ethyl, isopropyl, cyclopropyl, methoxy, ethoxy, methylthio, ethylthio, monofluoromethyl, difluoromethyl, trifluoromethyl, difluorochloromethyl, trichloromethyl, trifluoromethoxy, trichloromethoxy, trifluoromethylthio or difluoromethylthio and
R$^2$ represents hydrogen, fluorine, chlorine, bromine, iodine, methyl, ethyl, methoxy, ethoxy, methylthio or ethylthio and
R$^3$ represents hydrogen, methyl, ethyl, hydroxymethyl, hydroxyethyl, trifluoromethyl, difluoromethyl or phenyl.

A furthermore particularly preferably represents a radical of the formula

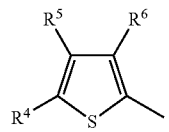

in which
R$^4$ and R$^5$ independently of one another represent hydrogen, fluorine, chlorine, bromine, methyl, ethyl, difluoromethyl, trifluoromethyl, difluorochloromethyl or trichloromethyl and
R$^6$ represents fluorine, chlorine, bromine, cyano, methyl, trifluoromethyl, trifluoromethoxy, difluoromethoxy, difluorochloromethoxy or trichloromethoxy.

A furthermore particularly preferably represents a radical of the formula

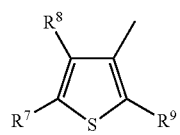

in which
R$^7$ and R$^8$ independently of one another represent hydrogen, fluorine, chlorine, bromine, methyl, ethyl, difluoromethyl, trifluoromethyl, difluorochloromethyl or trichloromethyl and
R$^9$ represents hydrogen, fluorine, chlorine, bromine, methyl or ethyl.

A furthermore particularly preferably represents a radical of the formula

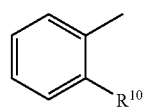

in which
R$^{10}$ represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

A furthermore particularly preferably represents a radical of the formula

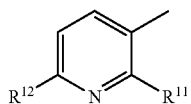

in which
R$^{11}$ represents fluorine, chlorine, bromine, iodine, hydroxyl, cyano, methyl, ethyl, n-propyl, isopropyl, n-butyl, isobutyl, sec-butyl, tert-butyl, methoxy, ethoxy, methylthio, ethylthio, trifluoromethyl, difluoromethyl, difluorochloromethyl, trichloromethyl, trifluoromethoxy, difluoromethoxy, difluorochloromethoxy, trichloromethoxy, difluoromethylthio, trifluoromethylthio and R$^{12}$ represents hydrogen, fluorine, chlorine, bromine, iodine, cyano, methyl, ethyl, n-propyl, isopropyl, n-butyl, isobutyl, sec-butyl, tert-butyl, methoxy, ethoxy, methylthio, ethylthio, methylsulfinyl, methylsulfonyl, trifluoromethyl, difluoromethyl, difluorochloromethyl, trichloromethyl, trifluoromethoxy, difluoromethoxy, difluorochloromethoxy or trichloromethoxy.

A furthermore particularly preferably represents a radical of the formula

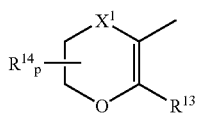

in which
R$^{13}$ represents methyl, ethyl, trifluoromethyl, difluoromethyl, difluorochloromethyl or trichloromethyl and
R$^{14}$ represents methyl or ethyl,
X$^{1}$ represents S (sulfur), represents SO, SO$_2$ or CH$_2$ and
p represents 0, 1 or 2.

A furthermore particularly preferably represents a radical of the formula

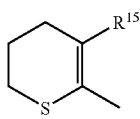

in which
R$^{15}$ represents methyl, ethyl, trifluoromethyl, difluoromethyl, difluorochloromethyl or trichloromethyl.

A furthermore particularly preferably represents a radical of the formula

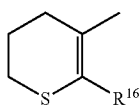

in which
R$^{16}$ represents methyl, ethyl, trifluoromethyl, difluoromethyl, difluorochloromethyl or trichloromethyl.

A furthermore particularly preferably represents a radical of the formula

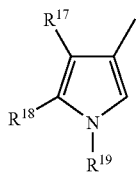

in which
R$^{17}$ represents fluorine, chlorine, bromine, cyano, methyl, ethyl, isopropyl, trifluoromethyl, difluoromethyl, difluorochloromethyl or trichloromethyl, R$^{18}$ represents hydrogen, fluorine, chlorine, bromine, methyl, ethyl, trifluoromethyl, difluoromethyl or trichloromethyl and R$^{19}$ represents hydrogen, methyl, ethyl, trifluoromethyl, methoxymethyl, ethoxymethyl, hydroxymethyl or hydroxyethyl.

A furthermore particularly preferably represents a radical of the formula

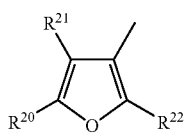

in which
R$^{20}$ and R$^{21}$ independently of one another represent hydrogen, fluorine, chlorine, bromine, methyl, ethyl, trifluoromethyl, difluoromethyl, difluorochloromethyl or trichloromethyl and R$^{22}$ represents hydrogen, fluorine, chlorine, bromine, methyl, ethyl, trifluoromethyl, difluoromethyl, difluorochloromethyl or trichloromethyl.

A furthermore particularly preferably represents a radical of the formula

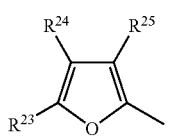

in which
R$^{23}$ and R$^{24}$ independently of one another represent hydrogen, fluorine, chlorine, bromine, nitro, methyl, ethyl, trifluoromethyl, difluoromethyl, difluorochloromethyl or trichloromethyl and R$^{25}$ represents hydrogen, fluorine, chlorine, bromine, methyl, ethyl, trifluoromethyl, difluoromethyl, difluorochloromethyl or trichloromethyl.

A furthermore particularly preferably represents a radical of the formula

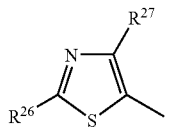

in which
- $R^{26}$ represents hydrogen, fluorine, chlorine, bromine, amino, methylamino, dimethylamino, cyano, methyl, ethyl, trifluoromethyl, difluoromethyl, difluorochloromethyl or trichloromethyl and
- $R^{27}$ represents fluorine, chlorine, bromine, methyl, ethyl, trifluoromethyl, difluoromethyl, difluorochloromethyl or trichloromethyl.

A furthermore particularly preferably represents a radical of the formula

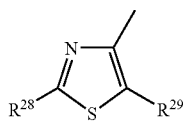

in which
- $R^{28}$ represents hydrogen, fluorine, chlorine, bromine, amino, methylamino, dimethylamino, cyano, methyl, ethyl, trifluoromethyl, difluoromethyl, difluorochloromethyl or trichloromethyl and
- $R^{29}$ represents fluorine, chlorine, bromine, methyl, ethyl, trifluoromethyl, difluoromethyl, difluorochloromethyl or trichloromethyl.

A furthermore particularly preferably represents a radical of the formula

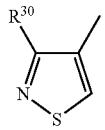

in which
- $R^{30}$ represents fluorine, chlorine, bromine, methyl, ethyl, trifluoromethyl, difluoromethyl, difluorochloromethyl or trichloromethyl.

A furthermore particularly preferably represents a radical of the formula

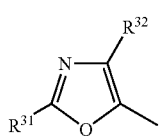

in which
- $R^{31}$ represents hydrogen, methyl or ethyl and
- $R^{32}$ represents fluorine, chlorine, bromine, methyl or ethyl.

A furthermore particularly preferably represents a radical of the formula

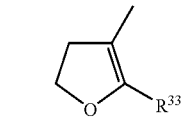

in which
- $R^{33}$ represents methyl, ethyl, trifluoromethyl, difluoromethyl, difluorochloromethyl or trichloromethyl.

A furthermore particularly preferably represents a radical of the formula

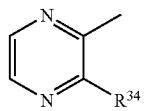

in which
- $R^{34}$ represents hydrogen, fluorine, chlorine, bromine, methyl, ethyl or trifluoromethyl.

R very particularly preferably represents hydrogen or methyl.

Z very particularly preferably represents allyl, 2-butenyl, 2-methylallyl, 1-methylallyl, 3-methyl-2-butenyl, propargyl, 2-butynyl, 2-methyl-3-butynyl, 3,3-difluoroallyl, cyclopropylmethyl.

X very particularly preferably represents fluorine or methyl.

Y very particularly preferably represents fluorine, chlorine, bromine, cyano, methyl, methoxy, methylthio, trichloromethyl, trifluoromethyl, trifluoromethoxy, trifluoromethylthio.

m very particularly preferably represents 0 or 1.

n very particularly preferably represents 0 or 1.

A very particularly preferably represents a radical of the formula

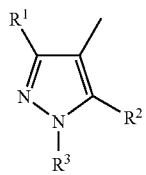

in which
- $R^1$ represents fluorine, chlorine, bromine, iodine, methyl, isopropyl, cyclopropyl, monofluoromethyl, difluoromethyl or trifluoromethyl and
- $R^2$ represents hydrogen, fluorine, chlorine or methyl and
- $R^3$ represents methyl.

A furthermore very particularly preferably represents a radical of the formula

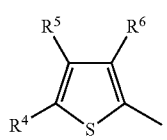

in which

R⁴ and R⁵ independently of one another represent hydrogen, fluorine or methyl and R⁶ represents methyl.

A furthermore very particularly preferably represents a radical of the formula

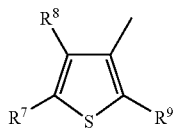

in which

R⁷ and R⁸ independently of one another represent hydrogen, fluorine or methyl and R⁹ represents methyl.

A furthermore very particularly preferably represents a radical of the formula

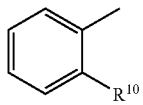

in which

R¹⁰ represents iodine, methyl, difluoromethyl or trifluoromethyl,

R¹⁰ furthermore represents chlorine or bromine.

A furthermore very particularly preferably represents a radical of the formula

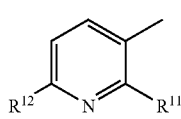

in which

R¹¹ represents fluorine, chlorine, bromine, methyl or trifluoromethyl and

R¹² represents hydrogen.

A furthermore very particularly preferably represents a radical of the formula

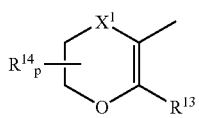

in which

R¹³ represents methyl or trifluoromethyl and

R¹⁴ represents methyl,

X¹ represents S (sulfur) or CH₂ and p represents 0 or 1.

A furthermore very particularly preferably represents a radical of the formula

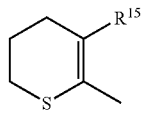

in which

R¹⁵ represents methyl, trifluoromethyl or difluoromethyl.

A furthermore very particularly preferably represents a radical of the formula

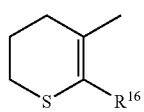

in which

R¹⁶ represents methyl, trifluoromethyl or difluoromethyl.

A furthermore very particularly preferably represents a radical of the formula

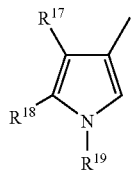

in which

R¹⁷ represents fluorine, methyl or trifluoromethyl,

R¹⁸ represents hydrogen or methyl and

R¹⁹ represents methyl or methoxymethyl.

A furthermore very particularly preferably represents a radical of the formula

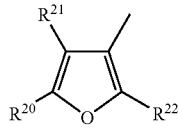

in which

R²⁰ and R²¹ independently of one another represent hydrogen, fluorine or methyl and R²² represents methyl or trifluoromethyl.

A furthermore very particularly preferably represents a radical of the formula

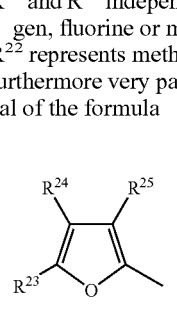

in which

R²³ and R²⁴ independently of one another represent hydrogen, fluorine or methyl and R²⁵ represents methyl.

A furthermore very particularly preferably represents a radical of the formula

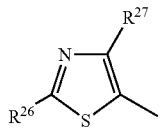

in which
R²⁶ represents fluorine, chlorine, amino or methyl and
R²⁷ represents chlorine, methyl, trifluoromethyl or difluoromethyl.

A furthermore very particularly preferably represents a radical of the formula

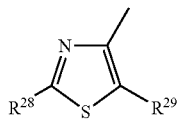

in which
R²⁸ represents fluorine, chlorine, amino or methyl and
R²⁹ represents chlorine, methyl, trifluoromethyl or difluoromethyl.

A furthermore very particularly preferably represents a radical of the formula

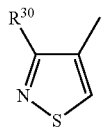

in which
R³⁰ represents chlorine, methyl, trifluoromethyl or difluoromethyl.

A furthermore very particularly preferably represents a radical of the formula

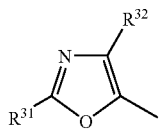

in which
R³¹ represents methyl and
R³² represents chlorine or methyl.

A furthermore very particularly preferably represents a radical of the formula

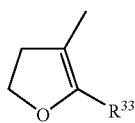

in which
R³³ represents methyl, trifluoromethyl or difluoromethyl.

A furthermore very particularly preferably represents a radical of the formula

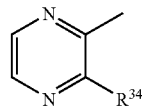

in which
R³⁴ represents hydrogen, chlorine or methyl.

R especially preferably represents hydrogen or methyl.
Z especially preferably represents allyl, 2-methyl-allyl, 1-methyl-allyl, 3-methyl-2-butenyl, propargyl, 2-butynyl, 3,3-difluoroallyl, cyclopropylmethyl.
X especially preferably represents fluorine.
m especially preferably represents 0 or 1.
n especially preferably represents 0.
A especially preferably represents a radical of the formula

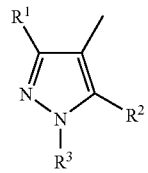

in which
R¹ represents methyl, monofluoromethyl, difluoromethyl or trifluoromethyl and
R² represents hydrogen, fluorine, chlorine or methyl and
R³ represents methyl.

A furthermore especially preferably represents a radical of the formula

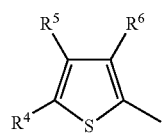

in which
R⁴ and R⁵ each represent hydrogen and
R⁶ represents methyl.

A furthermore especially preferably represents a radical of the formula

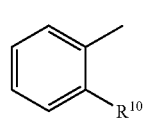

in which
R¹⁰ represents iodine, methyl or trifluoromethyl.

A furthermore especially preferably represents a radical of the formula

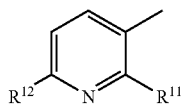

in which
R$^{11}$ represents chlorine or trifluoromethyl and
R$^{12}$ represents hydrogen.

A furthermore especially preferably represents a radical of the formula

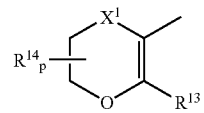

in which
R$^{13}$ represents methyl or trifluoromethyl and
X$^{1}$ represents S (sulfur) and
p represents 0.

A furthermore especially preferably represents a radical of the formula

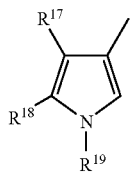

in which
R$^{17}$ represents methyl or trifluoromethyl,
R$^{18}$ represents hydrogen or methyl and
R$^{19}$ represents methyl.

A furthermore especially preferably represents a radical of the formula

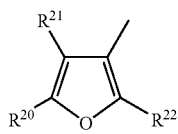

in which
R$^{20}$ and R$^{21}$ each represent hydrogen and
R$^{22}$ represents methyl.

A furthermore especially preferably represents a radical of the formula

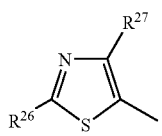

in which
R$^{26}$ represents amino or methyl and
R$^{27}$ represents methyl, trifluoromethyl or difluoromethyl.

A furthermore especially preferably represents a radical of the formula

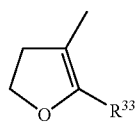

in which
R$^{33}$ represents methyl.

Preference is furthermore given to compounds of the formula (I-1)

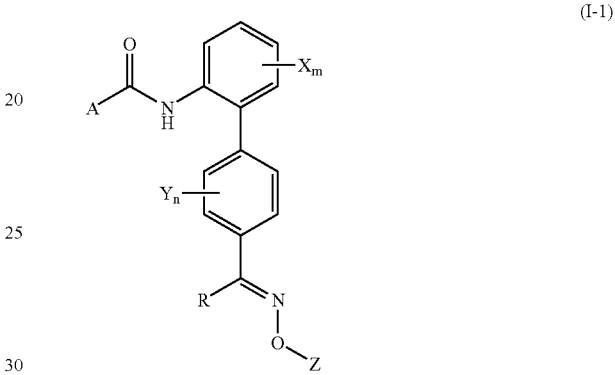

(I-1)

in which

R, Z, X, Y, m, n and A are as defined above. Suitable are in each case all combinations of the general, preferred, particularly preferred, very particularly preferred and especially preferred meanings mentioned above.

Particular preference is given to compounds of the formula (I-1) in which X is fluorine and m is 0 or 1.

Particular preference is given to compounds of the formula (I-1) in which n is 0.

Particular preference is given to compounds of the formula (I-1) in which R is hydrogen or methyl.

Particular preference is furthermore given to compounds of the formula (I) in which X is fluorine and m is 0 or 1.

Particular preference is furthermore given to compounds of the formula (I) in which n is 0.

Particular preference is furthermore given to compounds of the formula (I) in which R is hydrogen or methyl.

Preferred, particularly preferred, very particularly preferred and especially preferred are compounds which carry the substituents mentioned under preferred, particularly preferred, very particularly preferred and especially preferred, respectively.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different. A plurality of radicals having the same indices, such as, for example, m radicals X for m>1, can be identical or different.

Halogen-substituted radicals, such as, for example, haloalkyl, are mono- or polyhalogenated. In the case of polyhalogenation, the halogen atoms can be identical or different.

Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. The definitions apply both to the end products and, correspondingly, to precursors and intermediates. Moreover, individual definitions may not apply.

Using 5-fluoro-1,3-dimethyl-1H-pyrazole-4-carbonyl chloride and 1-(2'-aminobiphenyl-4-yl)ethanone O-allyl oxime as starting materials, the course of the process (a) according to the invention can be illustrated by the formula scheme below.

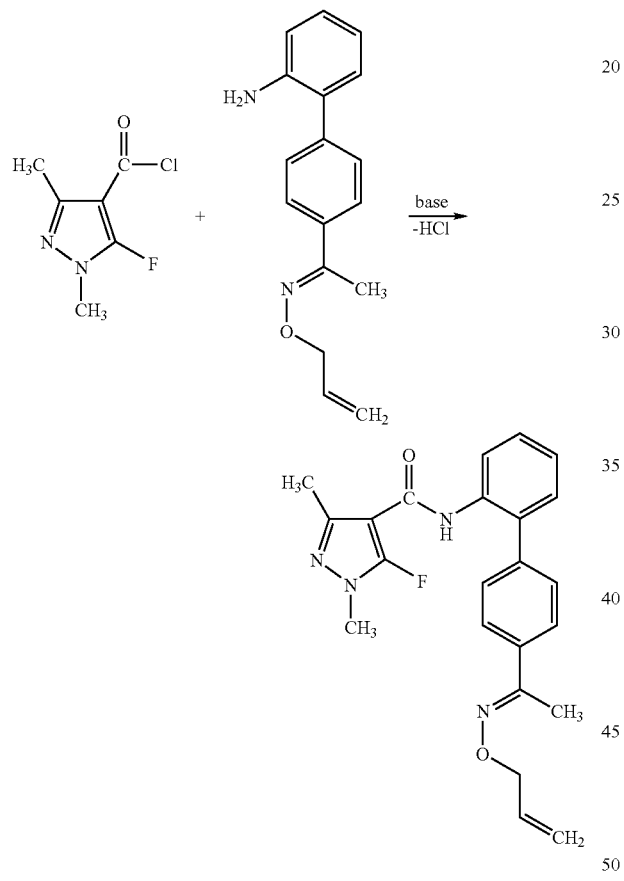

Using N-(2-iodophenyl)-5-fluoro-1,3-dimethyl-1H-pyrazole-4-carboxamide and 4-[1-(allyloxyimino)ethyl]phenylboronic acid as starting materials and a catalyst, the course of the process (b) according to the invention can be illustrated by the following scheme below.

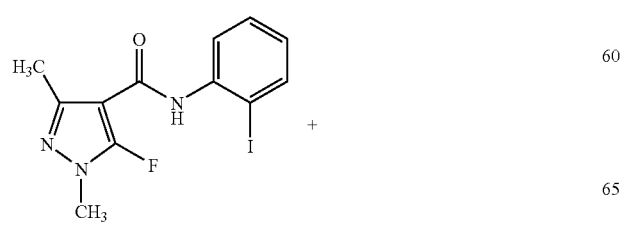

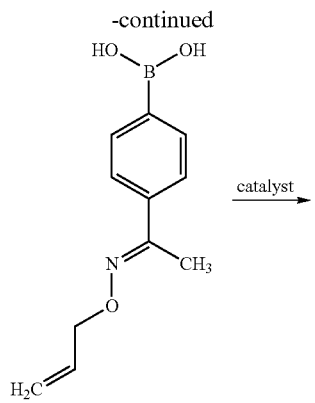

Using 2-[(5-fluoro-1,3-dimethylpyrazol-4-yl)carbonylamino]phenylboronic acid and 1-(4-bromophenyl)ethanone O-allyl oxime as starting materials and a catalyst, the course of the process (c) according to the invention can be illustrated by the formula scheme below.

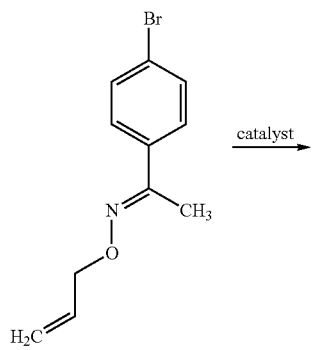

-continued

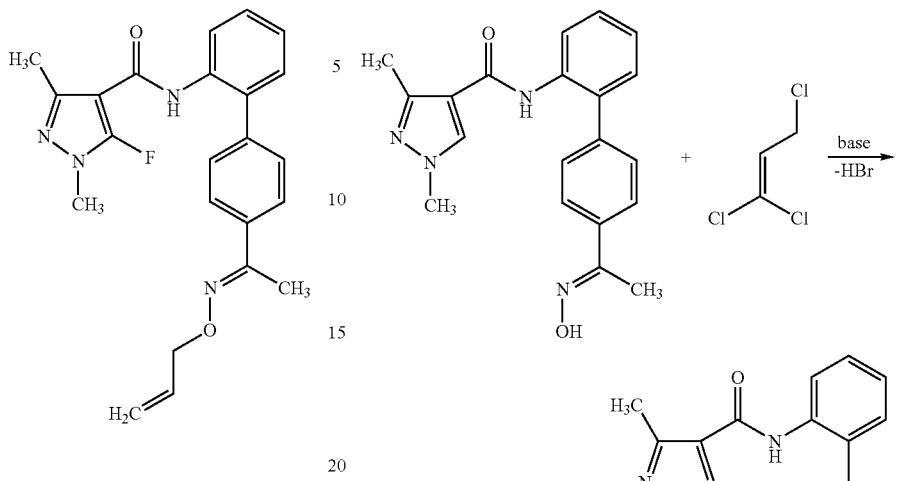

Using N-(4'-acetylbiphenyl-2-yl)-2-chloronicotinamide and O-(3,3-dichloroallyl)hydroxylamine hydrochloride as starting materials, the course of the process (d) according to the invention can be illustrated by the formula scheme below.

Using N-(4'-{1-[hydroxyimino]ethyl}biphenyl-2-yl) 1,3-dimethyl-1H-pyrazole-4-carboxamide and 1,1,3-trichloropropene as starting materials, the course of the process (e) according to the invention can be illustrated by the formula scheme below.

Using N-(2-bromophenyl)-5-fluoro-1,3-dimethyl-1H-pyrazole-4-carboxamide and 1-(4-bromophenyl)ethanone O-allyl oxime as starting materials and a catalyst and 4,4,4',4',5,5,5',5'-octamethyl-2,2'-bis-1,3,2-dioxaborolane, the course of the process (f) according to the invention can be illustrated by the formula scheme below.

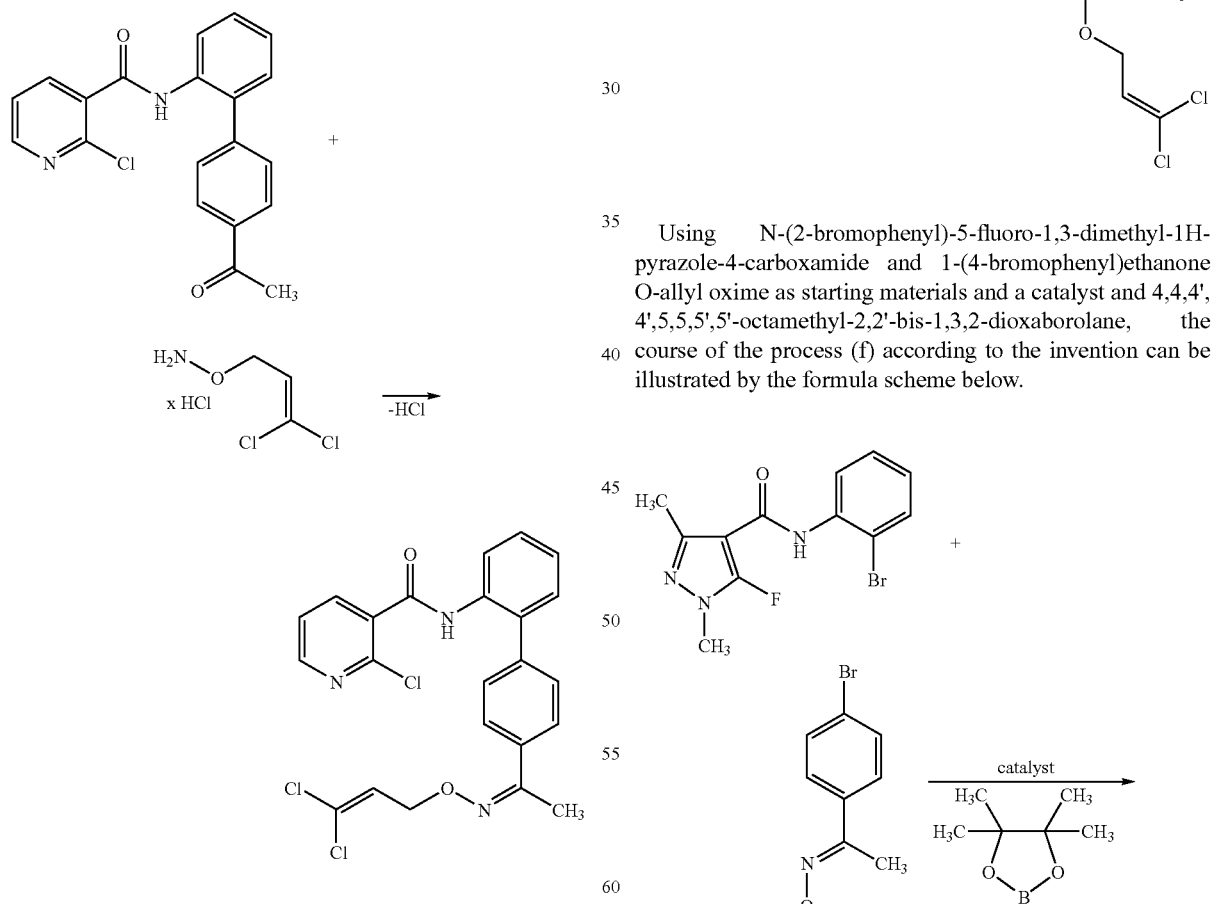

-continued

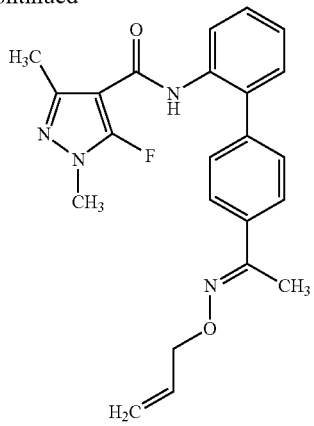

Illustration of the Processes and Intermediates

The formula (II) provides a general definition of the carboxylic acid derivatives required as starting materials for carrying out the process (a) according to the invention. In this formula, A preferably has those meanings which have already been mentioned in connection with the description of the compounds of the formula (I) according to the invention as being preferred, particularly preferred, very particularly preferred and especially preferred for these radicals. G preferably represents chlorine, bromine, hydroxyl, methoxy or ethoxy, particularly preferably chlorine, hydroxyl or methoxy.

The carboxylic acid derivatives of the formula (II) are known or can be prepared by known processes (cf. WO 93/11 117, EP-A 0 545 099, EP-A 0 589 301 and EP-A 0 589 313).

The formula (III) provides a general definition of the aniline derivatives required as reaction components for carrying out the process (a) according to the invention. In this formula, R, Z, X, Y, m and n preferably have those meanings which have already been mentioned in connection with the description of the compounds of the formula (I) according to the invention as being preferred, particularly preferred, very particularly preferred and especially preferred for these radicals or these indices.

The aniline derivatives of the formula (III) are novel. Some of them can be prepared by known methods (cf EP-A 0 545 099 and EP-A 0 589 301).

Aniline derivatives of the formula (III) are furthermore obtained when g) 2-haloaniline derivatives of the general formula (XI)

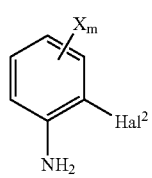

(XI)

in which
X and m are as defined above and
$Hal^2$ represents halogen are reacted with boronic acid derivatives of the formula (V)

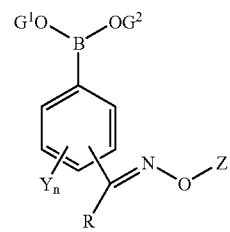

(V)

in which R, Z, Y, n, $G^1$ and $G^2$ are as defined above,
if appropriate in the presence of an acid binder, if appropriate in the presence of an inert organic diluent and if appropriate in the presence of catalyst, or h) anilineboronic acids of the formula (XII)

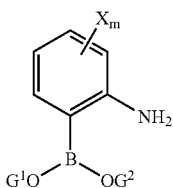

(XII)

in which X, m, $G^1$ and $G^2$ are as defined above
are reacted with phenyloxime derivatives of the formula (VII)

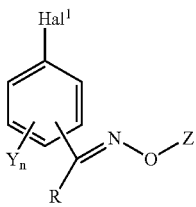

(VII)

in which R, Z, Y, n and $Hal^1$ are as defined above,
if appropriate in the presence of an acid binder, if appropriate in the presence of an inert organic diluent and if appropriate in the presence of a catalyst.

The formula (XI) provides a general definition of the 2-haloaniline derivatives required as reaction components for carrying out the processes (g) and (l) (see below) according to the invention. In this formula, X and m preferably have those meanings which have already been mentioned in connection with the description of the compounds of the formula (I) according to the invention as being preferred, particularly preferred, very particularly preferred and especially preferred for these radicals or these indices. Hal preferably represents fluorine, chlorine or bromine, particularly preferably chlorine or bromine.

The 2-haloaniline derivatives of the formula (XI) are commercially available or can be prepared from the corresponding nitro compounds by reduction.

The formula (XII) provides a general definition of the anilineboronic acids required as reaction components for carrying out the processes (h) and (j) (see below) according to the invention. In this formula, X and m preferably have those meanings which have already been mentioned in connection with the description of the compounds of the formula (I) according to the invention as being preferred, particularly preferred, very particularly preferred and especially preferred for these radicals or these indices. $G^1$ and $G^2$ preferably each represent hydrogen.

Anilineboronic acids of the formula (XII) are commercially available.

The formula (IV) provides a general definition of the carboxamide derivatives required as starting materials for carrying out the processes (b) and (f) according to the invention. In this formula, A, X and m preferably have those meanings which have already been mentioned in connection with the description of the compounds of the formula (I) according to the invention as being preferred, particularly preferred, very particularly preferred and especially preferred for these radicals or these indices.

The carboxamide derivatives of the formula (IV) are known or can be prepared by known processes (cf. WO 91/01311, EP-A 0 371 950).

The formula (V) provides a general definition of the boronic acid derivatives required for preparing the reaction components when carrying out the process (b) according to the invention and the process (g). In this formula, R, Z, Y and n preferably have those meanings which have already been mentioned in connection with the description of the compounds of the formula (I) according to the invention as being preferred, particularly preferred, very particularly preferred and especially preferred for these radicals or these indices. $G^1$ and $G^2$ preferably each represent hydrogen.

The boronic acid derivatives of the formula (V) are novel and can be prepared by i) reacting phenylboronic acids of the formula (XIII)

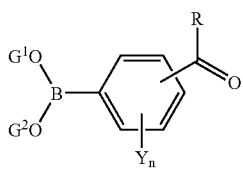

(XIII)

in which R, Y, n, $G^1$ and $G^2$ are as defined above
with hydroxylamine derivatives of the formula (IX)

Z—O—NH$_2$×HCl  (IX)

in which Z is as defined above,
if appropriate in the presence of an acid binder, if appropriate in the presence of an inert organic diluent and if appropriate in the presence of a catalyst.

The formula (XIII) provides a general definition of the phenylboronic acids required as reaction components for carrying out the processes (i) and (l) (see below) according to the invention. In this formula, R, Y and n preferably have those meanings which have already been mentioned in connection with the description of the compounds of the formula (I) according to the invention as being preferred, particularly preferred, very particularly preferred and especially preferred for these radicals or these indices. $G^1$ and $G^2$ preferably each represent hydrogen.

The phenylboronic acids of the formula (XIII) are commercially available.

The formula (VI) provides a general definition of the carboxamide boronic acid derivatives required as reaction components for carrying out the process (c) according to the invention. In this formula, A, X and m preferably have those meanings which have already been mentioned in connection with the description of the compounds of the formula (I) according to the invention as being preferred, particularly preferred, very particularly preferred and especially preferred for these radicals or these indices. $G^1$ and $G^2$ preferably each represent hydrogen or together represent tetramethylethylene.

The carboxamide boronic acid derivatives of the formula (VI) are novel. They can be prepared by j) reacting carboxylic acid derivatives of the formula (II)

(II)

in which A and G are as defined above
with anilineboronic acids of the formula (XII)

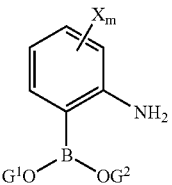

(XII)

in which X, m, $G^1$ and $G^2$ are as defined above,
if appropriate in the presence of an acid binder, if appropriate in the presence of an inert organic diluent and if appropriate in the presence of a catalyst.

The formula (VII) provides a general definition of the phenyloxime derivatives required as reaction components for carrying out the processes (c) and (f) according to the invention and the process (h). In this formula, R, Z, Y and n preferably have those meanings which have already been mentioned in connection with the description of the compounds of the formula (I) according to the invention as being preferred, particularly preferred, very particularly preferred and especially preferred for these radicals or these indices.

The phenyloxime derivatives of the formula (VII) are known and/or can be prepared by known processes (cf. Synth. Commun. 2000, 30, 665-669, Synth. Commun. 1999, 29, 1697-1701).

The formula (VIII) provides a general definition of the biphenylacyl derivatives required as starting materials for carrying out the process (d) according to the invention. In this formula, A, R, X, Y, m and n have those meanings which have already been mentioned in connection with the description of the compounds of the formula (I) according to the invention as being preferred, particularly preferred, very particularly preferred and especially preferred for these radicals or these indices.

The biphenylacyl derivatives of the formula (VIII) are novel. They can be prepared by k) reacting carboxylic acid derivatives of the formula (II)

(II)

in which A and G are as defined above
with 2-benzaldehydeaniline derivatives of the formula (XIV)

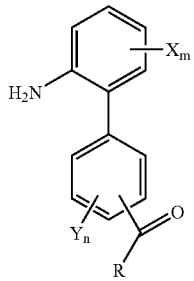
(XIV)

in which R, X, Y, m and n are as defined above,
if appropriate in the presence of an acid binder and if appropriate in the presence of an inert organic diluent.

The formula (XIV) provides a general definition of the 2-benzaldehydeaniline derivatives required as reaction components for carrying out the process (k) according to the invention. In this formula, R, X, Y, m and n preferably have those meanings which have already been mentioned in connection with the description of the compounds of the formula (I) according to the invention as being preferred, particularly preferred, very particularly preferred and especially preferred for these radicals or these indices.

The 2-benzaldehydeaniline derivatives of the formula (MV) are novel. They can be prepared by l) reacting aniline derivatives of the formula (XI)

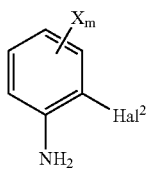
(XI)

in which X, m and Hal² are as defined above and
with phenylboronic acid derivatives of the formula (XIII)

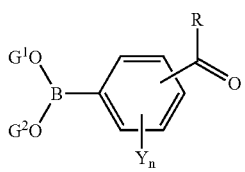
(XIII)

in which R, Y, n, $G^1$ and $G^2$ are as defined above,
if appropriate in the presence of an acid binder and if appropriate in the presence of an inert organic diluent.

The formula (IX) provides a general definition of the hydroxylamine derivatives required as reaction components for carrying out the process (d) according to the invention and the process (i). In this formula, Z preferably has those meanings which have already been mentioned in connection with the description of the compounds of the formula (I) according to the invention as being preferred, particularly preferred, very particularly preferred and especially preferred for this radical. Preference is given to using the hydrochlorides mentioned in the description. However, it is also possible to use the free hydroxylamine derivatives in the process according to the invention.

Hydroxylamine derivatives of the formula (IX) are commercially available.

The formula (I-a) provides a general definition of the hydroxyimino derivatives required as starting materials for carrying out the process (e) according to the invention. In this formula, A, R, X, Y, m and n preferably have those meanings which have already been mentioned in connection with the description of the compounds of the formula (I) according to the invention as being preferred, particularly preferred, very particularly preferred and especially preferred for these radicals or these indices.

The hydroxyimino derivatives of the formula (I-a) according to the invention can be prepared by one of the processes (a), (b), (c), (d) or (f) according to the invention described above.

The formula (X) provides a general definition of the compounds required as reaction components for carrying out the process (e) according to the invention. In this formula, Z preferably has those meanings which have already been mentioned in connection with the description of the compounds of the formula (I) according to the invention as being preferred, particularly preferred, very particularly preferred and especially preferred for this radical. E preferably represents chlorine, bromine, iodine, methanesulfonyl or p-toluenesulfonyl. E particularly preferably represents chlorine or bromine.

Compounds of the formula (X) are commercially available.

Suitable acid binders for carrying out the processes (a), (b), (c), (d), (e) and (f) according to the invention are in each case all inorganic and organic bases customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to operate without added acid binder or to use an excess of the amine component so that it simultaneously acts as acid binder.

Suitable diluents for carrying out the processes (a), (b), (c), (d), (e) and (f) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide, or sulfones, such as sulfolane.

When carrying out the processes (a), (b), (c), (d), (e) and (f) according to the invention, the reaction temperatures can in each case be varied within a relatively wide range. In general, the processes are carried out at temperatures between 0° C. and 140° C., preferably between 110° C. and 120° C.

The process (a), (b), (c), (d), (e) and (f) according to the invention are generally in each case carried out under atmospheric pressure. However, in each case it is also possible to operate under elevated or reduced pressure.

When carrying out the process (a) according to the invention, in general 1 mol or else an excess of aniline derivative of the formula (III) and from 1 to 3 mol of acid binder are employed per mole of acid halide of the formula (II). However, it is also possible to employ the reaction components in other ratios. Work-up is carried out by customary methods. In general, water is added to the reaction mixture and the organic phase is separated off and, after drying, concentrated under reduced pressure. The residue that remains may, if required, be freed of any impurities that may still be present using customary methods, such as chromatography or recrystallization.

When carrying out the process (b) according to the invention, in general 1 mol or else an excess of boronic acid derivative of the formula (V) and from 1 to 5 mol of acid binder are employed per mole of carboxamide of the formula (IV). However, it is also possible to employ the reaction components in other ratios. Work-up is carried out by customary methods. In general, water is added to the reaction mixture and the precipitate is separated off and dried. The residue that remains may, if required, be freed of any impurities that may still be present using customary methods, such as chromatography or recrystallization.

When carrying out the process (c) according to the invention, in general 1 mol or else an excess of phenyloxime derivative of the formula (VII) and from 1 to 10 mol of acid binder and from 0.5 to 5 mol % of a catalyst are employed per mole of carboxamide boronic acid derivative of the formula (VI). However, it is also possible to employ the reaction components in other ratios. Work-up is carried out by customary methods. In general, water is added to the reaction mixture and the precipitate is separated off and dried. The residue that remains may, if required, be freed of any impurities that may still be present using customary methods, such as chromatography or recrystallization.

When carrying out the process (d) according to the invention, in general 1 mol or else an excess of hydroxylamine derivative of the formula (IX) and from 1 to 5 mol of acid binder are employed per mole of biphenylacyl derivative of the formula (VIII). However, it is also possible to employ the reaction components in other ratios. Work-up is carried out by customary methods. In general, water is added to the reaction mixture and the precipitate is separated off, washed with water and diisopropyl ether and then dried. The residue that remains may, if required, be freed of any impurities that may still be present using customary methods, such as chromatography or recrystallization.

When carrying out the process (e) according to the invention, in general 1 mol or else an excess of reagent of the formula (X) and from 1 to 5 mol of acid binder are employed per mole of hydroxyimino derivative of the formula (I-a). However, it is also possible to employ the reaction components in other ratios. Work-up is carried out by customary methods. In general, water is added to the reaction mixture and the precipitate is separated off and dried. The residue that remains may, if required, be freed of any impurities that may still be present using customary methods, such as chromatography or recrystallization.

When carrying out the process (f) according to the invention, in general 1 mol or else an excess of phenyloxime derivative of the formula (VII) and from 1 to 5 mol of acid binder and from 1 to 5 mol of a catalyst are employed per mole of carboxamide derivative of the formula (IV). However, it is also possible to employ the reaction components in other ratios. Work-up is carried out by customary methods. In general, water is added to the reaction mixture and the precipitate is separated off and dried. The residue that remains may, if required, be freed of any impurities that may still be present using customary methods, such as chromatography or recrystallization.

The active compounds are suitable for protecting plants and plant organs, increasing harvest yields, improving the quality of the harvested material and controlling animal pests, in particular insects, arachnids and nematodes, which are encountered in agriculture, in forests, in gardens and in leisure facilities, in the protection of stored products and of materials, and in the hygiene sector and they are tolerated well by plants, have favorable homeotherm toxicity and good environmental compatibility. They may preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the *Dermaptera,* for example, *Forficula auricularia.*

From the order of the *Isoptera,* for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus,*

*Nilaparvata lugens, Aonidiella aurantii, Aspidiotus hederae, Pseudococcus* spp. and *Psylla* spp.

From the order of the *Lepidoptera*, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp. and *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus*.

From the order of the *Hymenoptera*, for example, *Diprion* spp., *Hoplocampa* spp., *Lasius* spp., *Monomorium pbaraonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the *Siphonaptera*, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The compounds according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea*
 (conidia form: *Drechslera*, syn: *Helminthosporium*);

*Cochliobolus* species, such as, for example, *Cochliobolus sativus*
 (conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, Botryfis cinerea;

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae;* and

*Pseudocercosporella* species, such as, for example, *Pseudocercosporella herpotrichoides*.

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance to these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling diseases in viticulture and in the cultivation of fruit and vegetables, such as, for example, against *Venturia, Botrytis, Sclerotina, Rhizoctonia, Uncinula, Sphaerotheca, Podosphaera, Alternaria* and *Colletotrichum* species. Rice diseases, such as *Pyricularia* and *Pellicularia* species, are likewise controlled with good results.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injection, and, in the case of propagation material, in particular in the case of seeds, also by applying one or more coats.

In the protection of materials, the substances according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes), and against slime organisms and algae.

Microorganisms of the following genera may be mentioned as examples:

*Alternaria*, such as *Alternaria tenuis,*
*Aspergillus*, such as *Aspergillus niger,*
*Chaetomium*, such as *Chaetomium globosum,*
*Coniophora*, such as *Coniophora puetana,*
*Lentinus*, such as *Lentinus tigrinus,*
*Penicillium*, such as *Penicillium glaucum,*
*Polyporus*, such as *Polyporus versicolor,*
*Aureobasidium*, such as *Aureobasidium pullulans,*
*Sclerophoma*, such as *Sclerophoma pityophila,*
*Trichoderma*, such as *Trichoderma viride,*
*Escherichia*, such as *Escherichia coli,*
*Pseudomonas*, such as *Pseudomonas aeruginosa*, and
*Staphylococcus*, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following compounds

Fungicides:

2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; fluberizimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesil); iodocarbi; ipconazole; iprobenfos; iprodione; iprovalicarb; irumamycin; isoprothiolane; isovaledione; kasugamycin; kresoximmethyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothalisopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofosmethyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulfate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nemaficides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulfone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, mnclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, tans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL40027, yl-5201, yl-5301, yl-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2, 2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

A mixture with other known active compounds, such as herbicides, or with fertilizers and growth regulators, safeners or semicochemicals, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidemmophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The compositions used for protecting industrial materials generally comprise the active compounds in an amount of from 1 to 95%, preferably from 10 to 75%.

The application concentrations of the active compounds according to the invention depend on the nature and the occurrence of the microorganisms to be controlled and on the composition of the material to be protected. The optimum amount for application can be determined by test series. In general, the application concentrations are in the range from 0.001 to 5% by weight, preferably from 0.05 to 1.0% by weight, based on the material to be protected.

The activity and the activity spectrum of the active compounds to be used according to the invention in the protection of materials, or of the compositions, concentrates or, quite generally, formulations preparable therefrom, can be increased, if appropriate, by addition of further antimicrobially active compounds, fungicides, bactericides, herbicides, insecticides or other active compounds for widening the activity spectrum or obtaining special effects such as, for example, additional protection against insects. These mixtures may have a wider activity spectrum than the compounds according to the invention.

When used as insecticides in their commercially available formulations and in the use forms prepared with these formulations, the active compounds according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared with these formulations, the active compounds according to the invention can furthermore be present in the form of a mixture with inhibitors which reduce the degradation of the active compound after application in the habitat of the plant, on the surface of parts of plants or in plant tissues.

The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound is distinguished by excellent residual action on wood and clay as well as good stability to alkali on limed substrates.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processabil ity of the harvested products. Further examples of such traits, examples which must be mentioned especially, are better defence of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defence of the plants against insects, arachnids, nematodes, and slugs and snails owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defence of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulfonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybean), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include also the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula (I) or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The preparation and the use of the active compounds according to the invention is illustrated by the examples below.

PREPARATION EXAMPLES

Example 1

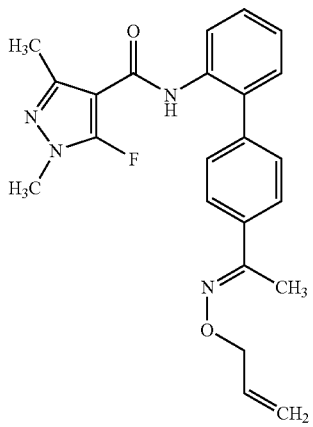
(compound 17)

Process (a)

0.300 g (1.126 mmol) of 1-(2'-aminobiphenyl-4-yl)ethanone O-allyl oxime and 0.114 g (1.126 mmol) of triethylamine are initially charged in 20 ml of toluene. At room temperature, 0.199 g (1.126 mmol) of 5-fluoro-1,3-dimethyl-1H-pyrazole-4-carbonyl chloride is added to the reaction mixture, and the mixture is stirred at 50° C. for 2 h. For work-up, the reaction mixture is cooled to room temperature, washed twice with in each case 100 ml of water, dried over sodium sulfate and concentrated under reduced pressure. The residue is recrystallized from n-hexane.

This gives 0.44 g (94.4% of theory) of N-(4'-{1-(allyloxy-imino)-ethyl}-biphenyl-2-yl)-5-fluoro-1,3-dimethyl-1H-pyrazole-4-carboxamide (compound 17, Table 1) of melting point 118° C.

Example 2

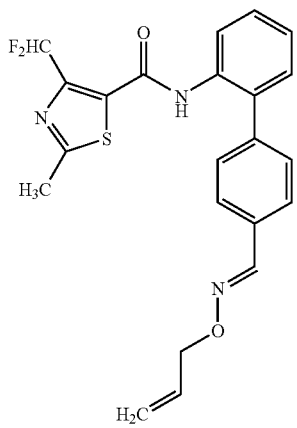
(compound 9)

Process (a)

0.300 g (1.000 mmol) of 2'-aminobiphenyl-4-carbaldehyde O-allyl oxime (III-1) and 0.120 g (1.000 mmol) of triethylamine are initially charged in 15 ml of toluene. At room temperature, 0.251 g (1.000 mmol) of 4-difluoromethyl-2-methylthiazole-5-carbonyl chloride, dissolved in 5 ml of toluene, is added to the reaction mixture, and the mixture is heated at 50° C. and stirred for 3 h. For work-up, the reaction mixture is cooled to room temperature and washed twice with in each case 80 ml of water, and the organic phase is dried over magnesium sulfate and then concentrated under reduced pressure. The residue is purified by silica gel column chromatography (hexane/methyl tert-butyl ether 3:1).

This gives 0.30 g (49.6% of theory) of N-[4'-(allyloxy-imino-methyl)-biphenyl-2-yl]-4-difluoromethyl-2-methylthiazole-5-carboxamide (compound 9, Table 1).

$^1$H-NMR (DMSO-D$_6$): δ=2.71 ppm (s, 3H)

Example 3

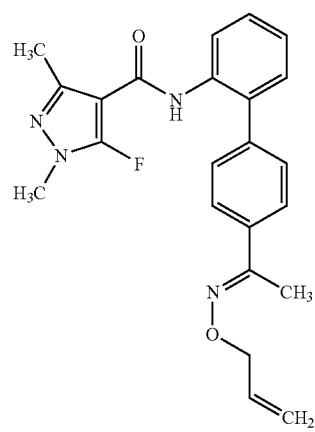
(compound 17)

Process (b)

At room temperature, 1.00 g (2.75 mmol) of N-(2-iodophenyl)-5-fluoro-1,3-dimethyl-1H-pyrazole-4-carboxamide, 0.61 g (2.78 mmol) of 4-[1-(allyloxyimino)ethyl]phenylboronic acid and 0.20 g of tetrakis(triphenylphosphine)palladium(0) are initially charged in 15 ml of dimethoxyethane. At room temperature, a solution of 1.18 g (11.14 mmol) of sodium carbonate in 15 ml of water is added with stirring. The mixture is heated at reflux temperature and stirred for 15 h. For work-up, the mixture is cooled to room temperature and extracted twice with in each case 50 ml of diethyl ether. The organic phases are washed with water, dried over sodium sulfate and concentrated under reduced pressure. The residue is purified by silica gel column chromatography (hexane/methyl tert-butyl ether 3:1).

This gives 0.13 g (10.5% of theory) of N-(4'-{1-(allyloxy-imino)ethyl}biphenyl-2-yl)-5-fluoro-1,3-dimethyl-1H-pyrazole-4-carboxamide (compound 17, Table 1) of logP (pH 2.3)=3.80.

49
Example 4

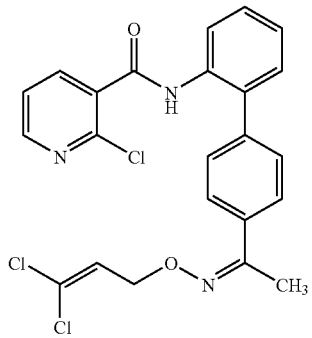

(compound 63)

Process (d)

0.79 g (2.24 mmol) of N-(4'-acetylbiphenyl-2-yl)-2-chloronicotinamide (VIII-1), 0.40 g (2.24 mmol) of O-(3,3-dichloroallyl)hydroxylamine hydrochloride and 0.22 g of sodium acetate are initially charged in a mixture of 5 ml of methanol and 2 ml of water and stirred at room temperature for 15 h. For work-up, the mixture is stirred into 30 ml of water and then extracted with 30 ml of dichloromethane. The organic phase is washed with 15 ml of water, and the phases are separated. The organic phase is dried over sodium sulfate and then concentrated under reduced pressure. The residue is triturated in a little hot hexane and cooled, and the residue is filtered off with suction.

This gives 0.68 g (63.9% of theory) of 2-chloro-N-{4'-[1-(3,3-dichloroallyloxyimino)ethyl]-biphenyl-2-yl}nicotinamide (compound 63, Table 1) of logP (pH 2.3)= 4.43.

50
Example 5

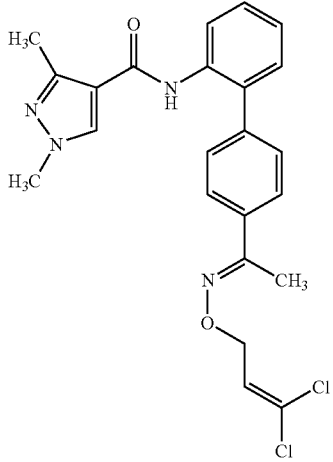

(compound 54)

Process (e)

At room temperature, 1.00 g (2.87 mmol) of N-{4'-[1-(hydroxyimino)ethyl]biphenyl-2-yl}-1,3-dimethyl-1H-pyrazole-4-carboxamide and 0.60 g of potassium carbonate (4.31 mmol) are initially charged in 50 ml of acetonitrile, and 0.417 g of 1,1,3-trichloropropene (2.870 mmol), dissolved in 5 ml of acetonitrile, are then added. The mixture is heated at reflux temperature and stirred for 15 h. For work-up, the mixture is cooled and filtered off with suction through a Nutsche filter, and the mother liquor is concentrated under reduced pressure. The residue is chromatographed on silica gel (hexane/acetone 9:1).

This gives 0.66 g (47.1% of theory) of N-(4'-{1-[3,3-dichloroallyloxyimino]ethyl}biphenyl-2-yl)-1,3-dimethyl-1H-pyrazole-4-carboxamide (compound 54, Table 1) as a solid of logP (pH 2.3)=3.97.

The biphenylcarboxamides of the formula (I-1) listed in the table below are likewise prepared according to Examples 1 to 5 and according to the general process descriptions and methods.

TABLE 1

(I-1)

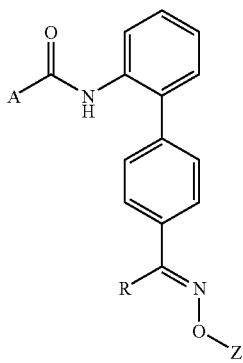

| No. | A | R | Z | logP (pH 2.3) | m.p. (° C.) |
|---|---|---|---|---|---|
| 1 | H3C-pyrazole(CH3)(F)(N-CH3) | H | —CH2-cyclopropyl | 3.77 | |

TABLE 1-continued
(I-1)
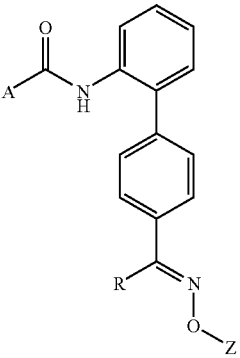
| No. | A | R | Z | logP (pH 2.3) | m.p. (° C.) |
|---|---|---|---|---|---|
| 2 | 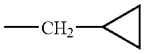 | H | —CH₂— | 4.16 | |
| 3 | 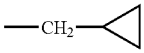 | H | —CH₂—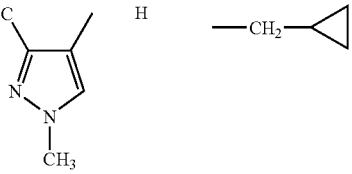 | 3.57 | |
| 4 | 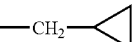 | H | —CH₂—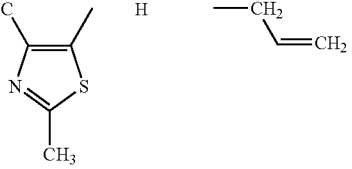 | 3.77 | |
| 5 | 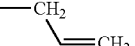 | H | —CH₂—CH=CH₂ | 3.91 | 107-109 |
| 6 | 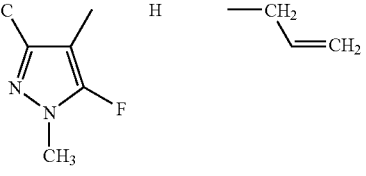 | H | —CH₂—CH=CH₂ | 3.47 | 88-90 |
| 7 | 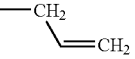 | H | —CH₂—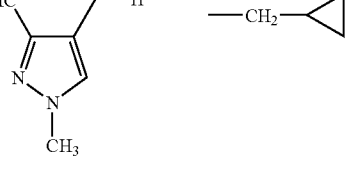 | 3.53 | |

TABLE 1-continued (I-1)

| No. | A | R | Z | logP (pH 2.3) | m.p. (° C.) |
|---|---|---|---|---|---|
| 8 | F₂HC— (2,5-dimethyl-thiazol-4-yl, with F₂HC and CH₃) | H | —CH₂—cyclopropyl | 3.87 | |
| 9 | F₂HC— (2,5-dimethyl-thiazol-4-yl) | H | —CH₂—CH=CH₂ | 3.65 | |
| 10 | F₂HC— (1,4-dimethyl-pyrazol-3-yl) | H | —CH₂—CH=CH₂ | 3.32 | |
| 11 | F₃C— (1,4-dimethyl-pyrazol-3-yl) | H | —CH₂—CH=CH₂ | 3.53 | 126 |
| 12 | 2-chloro-3-methyl-pyridin-4-yl | H | —CH₂—CH=CH₂ | 3.30 | 88-90 |
| 13 | H₃C— (1,4-dimethyl-5-fluoro-pyrazol-3-yl) | H | —CH₂—C≡CH | 3.04 | |
| 14 | 2-chloro-3-methyl-pyridin-4-yl | CH₃ | —CH₂—CH=CH₂ | 3.61 | 78-80 |

TABLE 1-continued (I-1)

[Structure: A-C(=O)-NH- attached to a biphenyl group, with the other phenyl bearing a C(R)=N-O-Z group]

| No. | A | R | Z | logP (pH 2.3) | m.p. (° C.) |
|---|---|---|---|---|---|
| 15 | 4-(F$_2$HC)-2,5-dimethyl-thiazol-yl | CH$_3$ | —CH$_2$—CH=CH$_2$ | 3.92 | 104-106 |
| 16 | 3-(F$_3$C)-1,4-dimethyl-pyrazol-yl | CH$_3$ | —CH$_2$—CH=CH$_2$ | 3.81 | 155 |
| 17 | 3,4-dimethyl-5-fluoro-1-methyl-pyrazol-yl (H$_3$C, with F) | CH$_3$ | —CH$_2$—CH=CH$_2$ | 3.80 | 118 |
| 18 | 3-(F$_2$HC)-1,4-dimethyl-pyrazol-yl | CH$_3$ | —CH$_2$—CH=CH$_2$ | 3.57 | 135-137 |
| 19 | 4-(F$_3$C)-2,5-dimethyl-thiazol-yl | CH$_3$ | —CH$_2$—CH=CH$_2$ | 4.19 | 126-128 |
| 20 | 2,3-dimethyl-thiophen-yl | CH$_3$ | —CH$_2$—CH=CH$_2$ | 4.54 | 76 |

TABLE 1-continued (I-1)

| No. | A | R | Z | logP (pH 2.3) | m.p. (° C.) |
|---|---|---|---|---|---|
| 21 | 2-CF₃-phenyl | CH₃ | —CH₂—CH=CH₂ | 4.31 | 118-120 |
| 22 | 2,3-dimethyl-5,6-dihydro-1,4-oxathiine | CH₃ | —CH₂-cyclopropyl | 4.69 | 78-79 |
| 23 | 2-chloro-3-methylpyridin-4-yl | CH₃ | —CH₂-cyclopropyl | 3.86 | 96-97 |
| 24 | 2,5-dimethyl-4-trifluoromethylthiazol-yl | CH₃ | —CH₂-cyclopropyl | 4.45 | 122-124 |
| 25 | 1,4-dimethyl-3-trifluoromethylpyrazol-5-yl | CH₃ | —CH₂-cyclopropyl | 4.05 | 149-150 |
| 26 | 5-fluoro-1,3,4-trimethylpyrazol-yl | CH₃ | —CH₂-cyclopropyl | 4.09 | 141-142 |
| 27 | 2-CF₃-phenyl | CH₃ | —CH₂-cyclopropyl | 4.56 | 115-116 |

TABLE 1-continued (I-1)

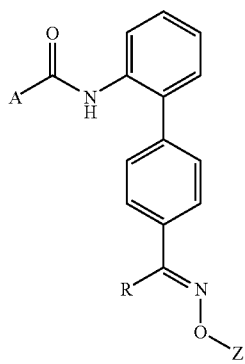

| No. | A | R | Z | logP (pH 2.3) | m.p. (° C.) |
|---|---|---|---|---|---|
| 28 | 2,3-dimethylfuran | CH$_3$ | —CH$_2$-cyclopropyl | 4.43 | 116-117 |
| 29 | 1,3-dimethyl-4-methylpyrazole | CH$_3$ | —CH$_2$-cyclopropyl | 3.42 | 142-144 |
| 30 | 1-methyl-4-methyl-3-trifluoromethylpyrrole | CH$_3$ | —CH$_2$-cyclopropyl | 3.82 | 154-155 |
| 31 | 1-methyl-4-methyl-3-trifluoromethylpyrrole | CH$_3$ | —CH$_2$—CH=CH$_2$ | 4.06 | 152 |
| 32 | 2,3-dimethylthiophene | CH$_3$ | —CH$_2$-cyclopropyl | 4.87 | 137-138 |
| 33 | 1-methyl-4-methyl-3-difluoromethylpyrazole | CH$_3$ | —CH$_2$-cyclopropyl | 3.82 | 170-171 |
| 34 | 2,5-dimethyl-4-difluoromethylthiazole | CH$_3$ | —CH$_2$-cyclopropyl | 4.19 | 132-133 |

TABLE 1-continued (I-1)

| No. | A | R | Z | logP (pH 2.3) | m.p. (° C.) |
|---|---|---|---|---|---|
| 35 | 3,4-dimethyl-1-methyl-pyrazol-5-yl | CH$_3$ | —CH$_2$—CH=CH$_2$ | 3.16 | 108-110 |
| 36 | 3,4-dimethyl-5-fluoro-1-methyl-pyrazol-5-yl | CH$_3$ | —CH$_2$—C(CH$_3$)=CH$_2$ | 4.18 | |
| 37 | 3,4-dimethyl-5-fluoro-1-methyl-pyrazol-5-yl | CH$_3$ | —CH$_2$—C≡C—CH$_3$ | 3.63 | |
| 38 | 2,3-dimethyl-furan-yl | CH$_3$ | —CH$_2$—CH=CH$_2$ | 4.14 | |
| 39 | 2,3-dimethyl-5,6-dihydro-1,4-oxathiin-yl | CH$_3$ | —CH$_2$—CH=CH$_2$ | 4.38 | |
| 40 | 3-trifluoromethyl-4-methyl-1-methyl-pyrazol-5-yl | CH$_3$ | —CH$_2$—C≡C—CH$_3$ | 3.67 | |
| 41 | 2-chloro-3-methyl-pyridin-yl | CH$_3$ | —CH$_2$—C≡C—CH$_3$ | 3.48 | |

TABLE 1-continued (I-1)

[Structure: A-C(=O)-NH- attached to a biphenyl system where the lower phenyl bears a C(R)=N-O-Z group]

| No. | A | R | Z | logP (pH 2.3) | m.p. (° C.) |
|---|---|---|---|---|---|
| 42 | 3-methyl-2-chloropyridin-yl | CH$_3$ | -CH(CH$_3$)-CH=CH$_2$ | 2.89 | |
| 43 | 2,3-dimethylthiophen-yl | CH$_3$ | -CH$_2$-C≡C-CH$_3$ | 4.33 | |
| 44 | 2-methyl-4-trifluoromethyl-5-methyl-thiazol-yl | CH$_3$ | -CH$_2$-C(CH$_3$)=CH$_2$ (with ethyl) | 3.49 | |
| 45 | 2,3-dimethylthiophen-yl | CH$_3$ | -CH(CH$_3$)-CH=CH$_2$ | 4.90 | |
| 46 | 3-trifluoromethyl-4-methyl-1-methyl-pyrazol-yl | CH$_3$ | -CH(CH$_3$)-CH=CH$_2$ | 4.15 | |
| 47 | 2-methyl-3-methyl-furan-yl | CH$_3$ | -CH(CH$_3$)-CH=CH$_2$ | 4.52 | |
| 48 | 3-trifluoromethyl-4-methyl-1-methyl-pyrazol-yl | CH$_3$ | -CH$_2$CH$_2$-C(CH$_3$)=CH$_2$ | 4.14 | |

TABLE 1-continued
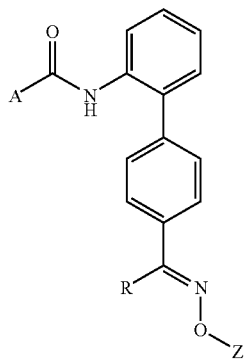
(I-1)
| No. | A | R | Z | logP (pH 2.3) | m.p. (° C.) |
|---|---|---|---|---|---|
| 49 | 2,3-dimethylthiophene | CH₃ | CH₂=C(CH₃)CH₂CH₃ (2-methylbut-1-en-... | 4.92 | |
| 50 | 2,3-dimethylfuran | CH₃ | —CH₂—C≡C—CH₃ | 3.95 | |
| 51 | 2,3-dimethylfuran | CH₃ | CH₂=C(CH₃)CH₂CH₃ | 4.51 | |
| 52 | 3,4-dimethyl-1-methylpyrazole | CH₃ | CH₂=C(CH₃)CH₂CH₃ | 3.52 | |
| 53 | 3,4-dimethyl-1-methylpyrazole | CH₃ | CH₂=CH—CH(CH₃)— | 3.53 | |
| 54 | 3,4-dimethyl-1-methylpyrazole | CH₃ | —CH₂—CH=CCl₂ | 3.97 | |
| 55 | 3,4-dimethyl-1-methylpyrazole | CH₃ | —CH₂—C≡C—CH₃ | 3.06 | |

TABLE 1-continued (I-1)

| No. | A | R | Z | logP (pH 2.3) | m.p. (° C.) |
|---|---|---|---|---|---|
| 56 | 2,3-dimethylthiophen-yl | CH₃ | —CH₂—CH=CCl₂ | 5.39 | |
| 57 | 1,4-dimethyl-3-(trifluoromethyl)pyrrol-yl | CH₃ | —CH(CH₃)—CH=CH₂ | 4.41 | |
| 58 | 2-(trifluoromethyl)phenyl | CH₃ | —CH₂—C(CH₃)=CH—CH₃ | 4.64 | |
| 59 | 2-(trifluoromethyl)phenyl | CH₃ | —CH(CH₃)—CH=CH₂ | 4.65 | |
| 60 | 2-chloro-3-methylpyridin-yl | CH₃ | —CH₂—C(CH₃)=CH—CH₃ | 3.95 | |
| 61 | 2,3-dimethylfuran-yl | CH₃ | —CH₂—CH=CCl₂ | 4.98 | |
| 62 | 2,5-dimethyl-4-(trifluoromethyl)thiazol-yl | CH₃ | —CH₂—CH=CCl₂ | 3.81 | |
| 63 | 2-chloro-3-methylpyridin-yl | CH₃ | —CH₂—CH=CCl₂ | 4.43 | |

TABLE 1-continued
(I-1)
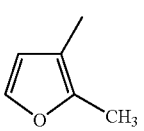
| No. | A | R | Z | logP (pH 2.3) | m.p. (° C.) |
|---|---|---|---|---|---|
| 64 | 2,3-dimethylfuran | CH₃ | —CH₂—C(CH₃)=CH—CH₃ | 4.84 | |
| 65 | 2-(trifluoromethyl)phenyl | CH₃ | —CH₂—CH=CCl₂ | 5.05 | |
| 66 | 1,4-dimethyl-3-(trifluoromethyl)pyrrole | CH₃ | —CH₂—CH=CCl₂ | 4.83 | |
| 67 | 2,5-dimethyl-4-(trifluoromethyl)thiazole | CH₃ | —CH₂—C≡CH | 3.72 | 108 |
| 68 | 2-chloro-3-methylpyridine | CH₃ | —CH₂—C≡CH | 3.16 | 130-132 |
| 69 | 4-(difluoromethyl)-2,5-dimethylthiazole | CH₃ | —CH₂—C≡CH | 3.45 | 113-115 |
| 70 | 1,4-dimethyl-3-(trifluoromethyl)pyrazole | CH₃ | —CH₂—C≡CH | 3.36 | 137-138 |

TABLE 1-continued
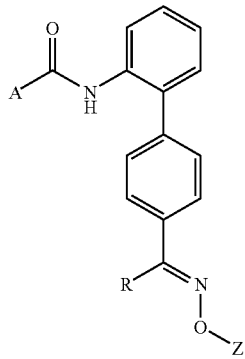
(I-1)
| No. | A | R | Z | logP (pH 2.3) | m.p. (° C.) |
|---|---|---|---|---|---|
| 71 | H₃C, CH₃ on pyrazole with F, N-CH₃ | CH₃ | —CH₂—≡CH | 3.27 | 109 |
| 72 | F₂HC, CH₃ on pyrazole, N-CH₃ | CH₃ | —CH₂—≡CH | 3.14 | 107 |
| 73 | CF₃-phenyl (ortho) | CH₃ | —CH₂—≡CH | 3.83 | 140-142 |
| 74 | dihydrodioxine with CH₃, CH₃ (S, O) | CH₃ | —CH₂—≡CH | 3.81 | 108-110 |
| 75 | F₃C, CH₃ on pyrrole, N-CH₃ | CH₃ | —CH₂—≡CH | 3.6 | 131-133 |
| 76 | 2,3-dimethylthiophene | CH₃ | —CH₂—≡CH | 3.94 | 109-110 |
| 77 | 2,3-dimethylfuran | CH₃ | —CH₂—≡CH | 3.59 | |

TABLE 1-continued
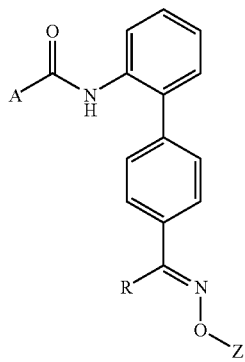
(I-1)
| No. | A | R | Z | logP (pH 2.3) | m.p. (° C.) |
|---|---|---|---|---|---|
| 78 | 1,3,4-trimethylpyrazol-5-yl (H₃C, CH₃, N-N-CH₃) | CH₃ | —CH₂—C≡CH | 2.75 | 98-101 |
| 79 | 2-iodophenyl | CH₃ | —CH₂—C≡CH | 3.81 | 122 |
| 80 | 2-bromophenyl | CH₃ | —CH₂—C≡CH | 3.74 | 116-118 |
| 81 | 2-chlorophenyl | CH₃ | —CH₂—C≡CH | 3.73 | 120 |
| 82 | 2-chloro-3-methylpyridin-yl | H | —CH₂—C≡CH | 2.92 | 126-128 |
| 83 | 2,5-dimethyl-4-trifluoromethylthiazol-yl | H | —CH₂—C≡CH | 3.48 | |

Preparation of Starting Materials of the Formula (III)

Example (III-1)

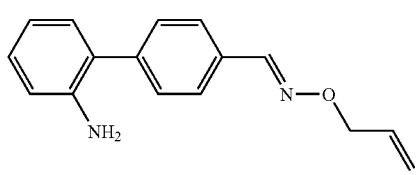

(III-1)

16.50 g (80.48 mmol) of 4-allyloxyiminomethylphenylboronic acid (V-1) and 13.84 g (80.48 mmol) of 2-bromoaniline together with 0.50 g (0.43 mmol) of tetrakis(triphenylphosphine)palladium are initially charged in a mixture of 100 ml of 1,2-dimethoxyethane and 100 ml of water. After addition of 34.12 g (321.92 mmol) of sodium carbonate, the mixture is heated at reflux for 12 h. For work-up, the reaction mixture is cooled to room temperature and extracted twice with in each case 200 ml of diethyl ether. The combined ether phases are washed with 400 ml of water and then dried over magnesium sulfate and concentrated under reduced pressure. The residue is chromatographed on silica gel (hexane/methyl tert-butyl ether 3:1).

This gives 4.3 g (15% of theory) of 2'-aminobiphenyl-4-carbaldehyde O-allyl oxime.

$^1$H-NMR (DMSO-D$_6$): δ=8.33 ppm (s, 1H)

Preparation of Starting Materials of the Formula (V)

Example (V-1)

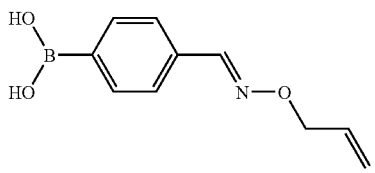

(V-1)

In a mixture of 100 ml of methanol and 40 ml of water, 13.69 g (91.28 mmol) of formylphenylboronic acid, 10.0 g of O-allylhydroxylamine hydrochloride (91.28 mmol) and 9.36 g (114.10 mmol) of sodium acetate are stirred at room temperature for 12 h. For work-up, the mixture is concentrated under reduced pressure and the residue is triturated with 150 ml of water, filtered off with suction through a glass frit, washed with a little water and dried on a clay disk.

This gives 16.5 g (84.6% of theory) of 4-allyloxyiminomethylphenylboronic acid.

$^1$H-NMR (DMSO-d$_6$): δ=8.27 ppm (s, 1H)

Preparation of Starting Materials of the Formula (VIII)

Example (VIII-1)

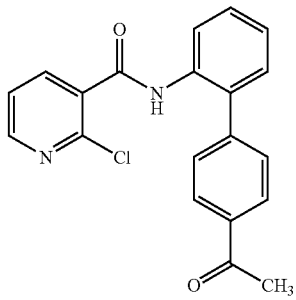

(VIII-1)

At room temperature, 8.33 g (47.33 mmol) of 2-chloronicotinoyl chloride, dissolved in 20 ml of toluene, are added over a period of 5 minutes to 10.00 g (47.33 mmol) of 1-(2'-aminobiphenyl-4-yl)ethanone (XIV-1) and 4.79 g (47.33 mmol) of triethylamine, dissolved in 150 ml of toluene. The mixture is heated at 50° C. and allowed to react for 10 h. For work-up, the mixture is cooled, 100 ml of water are added and the phases are separated. The organic phase is dried over sodium sulfate and concentrated under reduced pressure. The residue is recrystallized from n-hexane.

This gives 13.7 g (82.3% of theory) of N-(4'-acetyl-biphenyl-2-yl)-2-chloronicotinamide of logP (pH 2.3)=2.12.

Preparation of Starting Materials of the Formula (XIV)

Example (XIV-1)

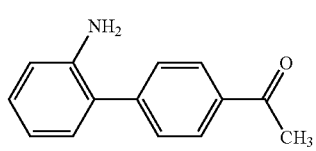

(XIV-1)

15.74 g (91.48 mmol) of 2-bromoaniline, 15.00 g of 4-acetylphenylboronic acid (91.48 mmol) and 0.529 g of tetrakis(triphenylphosphine)palladium(0) (0.457 mmol) are initially charged in 150 ml of dimethoxyethane. 38.78 g (365.93 mmol) of sodium carbonate, dissolved in 150 ml of water, are added over a period of 5 minutes. The mixture is heated at reflux temperature and stirred for 15 h. For work-up, the mixture is cooled and extracted twice with in each case 150 ml of ether. The combined organic phases are washed with water, dried over sodium sulfate and concentrated under reduced pressure. The residue is purified by silica gel column chromatography (cyclohexane/ethyl acetate 3:1).

This gives 15.0 g (72.6% of theory) of 1-(2'-aminobiphenyl-4-yl)ethanone of logP (pH 2.3)=1.80.

The logP values given in Table 1 were determined with EEC Directive 79/831 Annex V.A8 by HPLC (High Performance Liquid Chromatography) on a reverse-phase column (C 18). Temperature: 43° C.

Mobile phases for the determination in the acidic range (pH 2.3): 0.1% aqueous phosphoric acid, acetonitrile; linear gradient from 10% acetonitrile to 90% acetonitrile. Calibration was carried out using unbranched alkan-2-ones (having 3 to 16 carbon atoms) with known logP values (determination of the logP values by the retention times using linear interpolation between two successive alkanones).

The lambda-max values were determined in the maxima of the chromatographic signals using the UV spectra from 200 nm to 400 nm.

USE EXAMPLES

Example A

*Venturia* Test (Apple)/Protective

| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples show good activity:

TABLE A

Venturia test (apple)/protective

| | Active compound | Active compound application rate in g/ha | Efficacy in % |
|---|---|---|---|
| 1 | [structure] | 100 | 98 |
| 4 | [structure] | 100 | 91 |
| 6 | [structure] | 100 | 97 |

TABLE A-continued

Venturia test (apple)/protective

| | Active compound | Active compound application rate in g/ha | Efficacy in % |
|---|---|---|---|
| 5 | F₃C-thiazole(CH₃)-C(O)NH-biphenyl-CH=N-O-CH₂-CH=CH₂ | 100 | 100 |
| 13 | F₃C-pyrazole(N-CH₃, F)-C(O)NH-biphenyl-CH=N-O-CH₂-C≡CH | 100 | 100 |
| 7 | F₂HC-pyrazole(N-CH₃)-C(O)NH-biphenyl-CH=N-O-CH₂-cyclopropyl | 100 | 100 |
| 8 | F₂HC-thiazole(CH₃)-C(O)NH-biphenyl-CH=N-O-CH₂-cyclopropyl | 100 | 100 |
| 9 | F₂HC-thiazole(CH₃)-C(O)NH-biphenyl-CH=N-O-CH₂-CH=CH₂ | 100 | 100 |

TABLE A-continued

Venturia test (apple)/protective

| Active compound | | Active compound application rate in g/ha | Efficacy in % |
|---|---|---|---|
| 10 | [Structure: pyrazole with F₂HC, N-CH₃, carboxamide linked to biphenyl with CH=N-O-CH₂-CH=CH₂] | 100 | 100 |

Example B

Botrytis Test (Bean)/Protective

| Solvents: | 24.5 parts by weight of acetone |
|---|---|
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

In this test, for example, the following compounds according to the invention of the Preparation Examples show good activity:

TABLE B

Botrytis test (bean)/protective

| Active compound | | Active compound application rate in g/ha | Efficacy in % |
|---|---|---|---|
| 2 | [Structure: thiazole with F₃C, CH₃, carboxamide linked to biphenyl with CH=N-O-CH₂-cyclopropyl] | 500 | 98 |
| 3 | [Structure: 2-chloropyridine-3-carboxamide linked to biphenyl with CH=N-O-CH₂-cyclopropyl] | 500 | 95 |

TABLE B-continued

Botrytis test (bean)/protective

| Active compound | | Active compound application rate in g/ha | Efficacy in % |
|---|---|---|---|
| 6 | (structure) | 500 | 98 |
| 5 | (structure) | 500 | 83 |
| 13 | (structure) | 500 | 100 |
| 7 | (structure) | 500 | 96 |
| 8 | (structure) | 500 | 85 |

TABLE B-continued

Botrytis test (bean)/protective

| | Active compound | Active compound application rate in g/ha | Efficacy in % |
|---|---|---|---|
| 9 | F₂HC-thiazole-C(=O)NH-biphenyl-CH=N-O-CH₂-CH=CH₂ (2-methyl thiazole) | 500 | 95 |
| 10 | F₂HC-pyrazole(N-CH₃)-C(=O)NH-biphenyl-CH=N-O-CH₂-CH=CH₂ | 500 | 95 |

Example C

*Alternaria* Test (Tomato)/Protective

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and then remain at 100% relative atmospheric humidity and 20° C. for 24 hours. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

In this test, for example, the following compounds according to the invention of the Preparation Examples show good activity:

TABLE C

Alternaria test (tomato)/protective

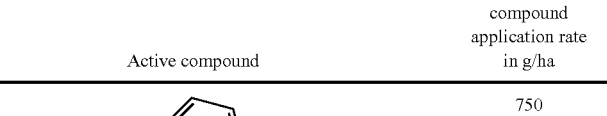

| | Active compound | Active compound application rate in g/ha | Efficacy in % |
|---|---|---|---|
| 1 | | 750 | 90 |

TABLE C-continued
Alternaria test (tomato)/protective
| Active compound | | Active compound application rate in g/ha | Efficacy in % |
|---|---|---|---|
| 2 | 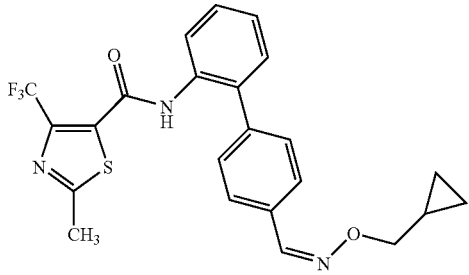 | 750 | 90 |
| 6 | 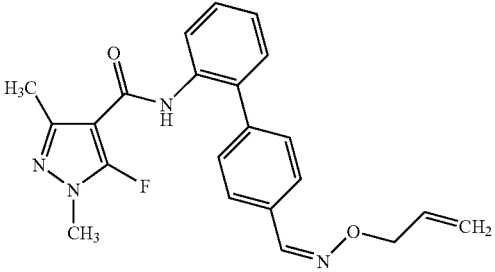 | 750 | 100 |
| 5 | 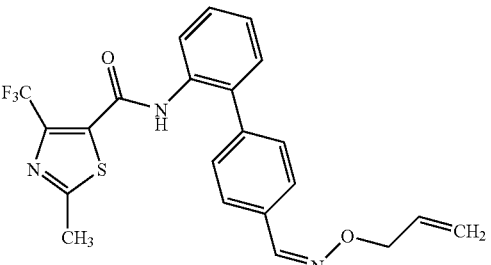 | 750 | 100 |
| 11 | 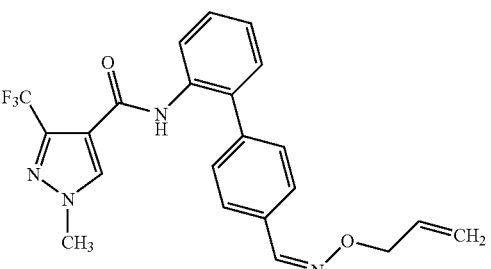 | 750 | 100 |
| 12 | 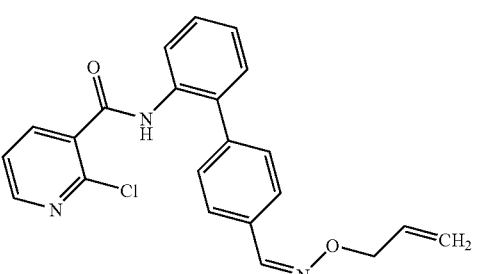 | 750 | 100 |

Example D

Puccinia Test (Wheat)/Protective

| Solvents: | 25 parts by weight of N,N-dimethylacetamide |
|---|---|
| Emulsifier: | 0.6 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spray coating has dried on, the plants are sprayed with the preparation of active compound at the stated application rate. The plants remain in an incubation cabin at 20° C. and 100% relative atmospheric humidity for 24 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples show good activity:

TABLE D

Puccinia test (wheat)/protective

| | Active compound | Active compound application rate in g/ha | Efficacy in % |
|---|---|---|---|
| 1 | [pyrazole-carboxamide structure with $H_3C$, $CH_3$, F, biphenyl, O-CH$_2$-cyclopropyl oxime] | 500 | 100 |
| 6 | [pyrazole-carboxamide structure with $H_3C$, $CH_3$, F, biphenyl, O-CH$_2$-CH=CH$_2$ oxime] | 500 | 100 |
| 7 | [pyrazole-carboxamide structure with $F_2HC$, $CH_3$, biphenyl, O-CH$_2$-cyclopropyl oxime] | 500 | 100 |

TABLE D-continued

Puccinia test (wheat)/protective

| Active compound | Active compound application rate in g/ha | Efficacy in % |
|---|---|---|
| 10 [structure: 3-difluoromethyl-1-methyl-pyrazole-4-carboxamide-N-(biphenyl-2-yl) with 4'-CH=N-O-CH2-CH=CH2] | 500 | 100 |
| 15 [structure: 4-difluoromethyl-2-methyl-thiazole-5-carboxamide-N-(biphenyl-2-yl) with 4'-C(CH3)=N-O-CH2-CH=CH2] | 500 | 100 |
| 40 [structure: 3-trifluoromethyl-1-methyl-pyrazole-4-carboxamide-N-(biphenyl-2-yl) with 4'-C(CH3)=N-O-CH2-C≡C-CH3] | 500 | 100 |
| 55 [structure: 3,1-dimethyl-pyrazole-4-carboxamide-N-(biphenyl-2-yl) with 4'-C(CH3)=N-O-CH2-C≡C-CH3] | 500 | 100 |

TABLE D-continued

Puccinia test (wheat)/protective

| | Active compound | Active compound application rate in g/ha | Efficacy in % |
|---|---|---|---|
| 69 | 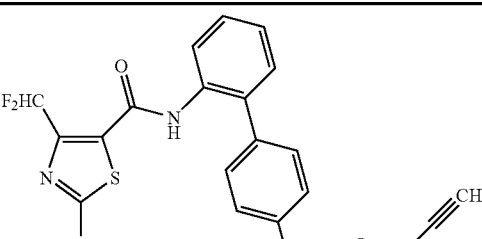 | 500 | 100 |
| 72 | 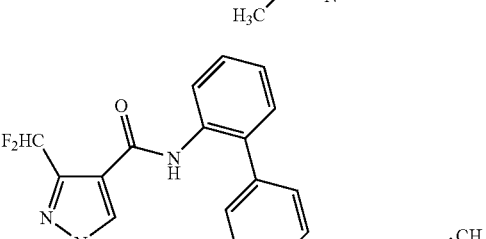 | 500 | 100 |

Example E

Plutella Test

| Solvents: | 100 parts by weight of acetone |
|---|---|
| | 1900 parts by weight of methanol |

To produce a suitable preparation of active compound, 1 part by weight of active compound is mixed with the stated amount of solvent, and the concentrate is diluted with methanol to the desired concentrations.

A stated amount of the preparation of active compound of the desired concentration is pipetted onto a standardized amount of synthetic feed. After the methanol has evaporated, about 200-300 eggs of the diamond back moth (*Plutella xylostella*) are placed onto the feed.

After the desired period of time, the kill of the eggs in % is determined. 100% means that all animals have been killed; 0% means that none of the animals have been killed.

In this test, for example, the following compounds of the Preparation Examples show good activity:

TABLE E

Plutella test

| | Active compound | Active compound concentration in ppm | Kill rate in % after $7^d$ |
|---|---|---|---|
| 15 | | 1000 | 95 |

TABLE E-continued

Plutella test

| Active compound | Active compound concentration in ppm | Kill rate in % after 7$^d$ |
|---|---|---|
| 22 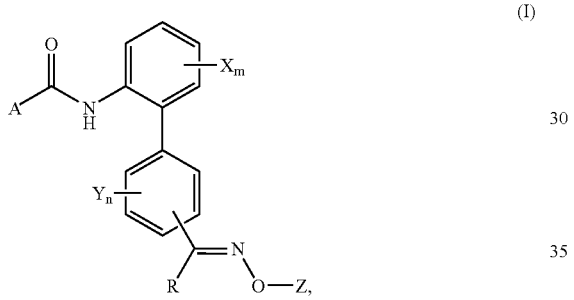 | 1000 | 95 |

What is claimed is:

1. A biphenylcarboxamide of formula (I)

(I)

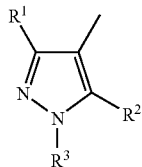

in which

R represents hydrogen or $C_1$-$C_6$-alkyl; or represents $C_1$-$C_3$-haloalkyl having 1 to 7 fluorine, chlorine, and/or bromine atoms, Z represents $C_3$-$C_8$-alkenyl or $C_3$-$C_8$-alkynyl; represents $C_3$-$C_8$-haloalkenyl or $C_3$-$C_8$-haloalkynyl having 1 to 5 fluorine, chlorine, and/or bromine atoms; or represents ($C_3$-$C_8$-cycloalkyl)($C_1$-$C_4$-alkyl), X and Y independently of one another represent halogen, cyano, nitro, $C_1$-$C_8$-alkyl, $C_1$-$C_8$-alkoxy, or $C_1$-$C_8$-alkylthio, or represent $C_1$-$C_6$-haloalkyl, $C_1$-$C_6$-haloalkoxy, or $C_1$-$C_6$-haloalkylthio having 1 to 13 fluorine, chlorine, and/or bromine atoms, m represents 0, 1, 2, 3, or 4, with the proviso that X represents identical or different radicals when m represents 2, 3, or 4, n represents 0, 1, 2, 3, or 4, with the proviso that Y represents identical or different radicals when n represents 2, 3, or 4, and A represents (i) a radical of the formula

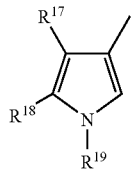

in which $R^1$ represents hydrogen, cyano, halogen, nitro, $C_1$-$C_4$-alkyl, $C_3$-$C_6$-cycloalkyl, $C_1$-$C_4$-alkoxy, $C_1$-$C_4$-alkylthio, aminocarbonyl, or aminocarbonyl-$C_1$-$C_4$-alkyl; or represents $C_1$-$C_4$-haloalkyl, $C_1$-$C_4$-haloalkoxy, or $C_1$-$C_4$-haloalkylthio having 1 to 5 halogen atoms, $R_2$ represents hydrogen, halogen, cyano, $C_1$-$C_4$-alkyl, $C_1$-$C_4$-alkoxy, or $C_1$-$C_4$-alkylthio, and $R_3$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, or $C_1$-$C_4$-alkoxy-$C_1$-$C_4$-alkyl; represents $C_1$-$C_4$-haloalkyl, halo($C_1$-$C_4$-alkylthio-$C_1$-$C_4$-alkyl), or halo($C_1$-$C_4$-alkoxy-$C_1$-$C_4$-alkyl) having 1 to 5 halogen atoms; or represents phenyl, or (ix) a radical of the formula in which $R^{17}$ represents halogen, cyano, $C_1$-$C_4$-alkyl or represents $C_1$-$C_4$-haloalkyl having 1 to 5 halogen atoms, $R^{18}$ represents hydrogen, halogen, or $C_1$-$C_4$-alkyl; or represents $C_1$-$C_4$-haloalkyl having 1 to 5 halogen atoms, and $R^{19}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkysulfonyl, di($C_1$-$C_4$-alkyl)aminosulfonyl, $C_1$-$C_6$-alkylcarbonyl; or represents optionally substituted phenylsulfonyl or benzoyl, or (xii) a radical of the formula

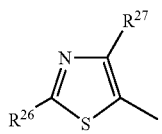

in which
R$^{26}$ represents hydrogen, halogen, amino, C$_1$-C$_4$-alkylamino, di(C$_1$-C$_4$-alkyl)amino, cyano, or C$_1$-C$_4$-alkyl; or represents C$_1$-C$_4$-haloalkyl having 1 to 5 halogen atoms, and R$^{27}$ represents halogen, C$_1$-C$_4$-alkyl, or C$_1$-C$_4$-haloalkyl having 1 to 5 halogen atoms, or (xiii) a radical of the formula

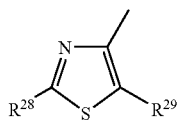

in which
R$^{28}$ represents hydrogen, halogen, amino, C$_1$-C$_4$-alkylamino, di(C$_1$-C$_4$-alkyl)amino, cyano, or C$_1$-C$_4$-alkyl; or represents C$_1$-C$_4$-haloalkyl having 1 to 5 halogen atoms, and R$^{29}$ represents halogen, C$_1$-C$_4$-alkyl, or C$_1$-C$_4$-haloalkyl having 1 to 5 halogen atoms, or (xiv) a radical of the formula

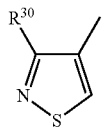

in which R$^{30}$ represents halogen, C$_1$-C$_4$-alkyl, or C$_1$-C$_4$-haloalkyl having 1 to 5 halogen atoms, or (xv) a radical of the formula

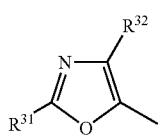

in which
R$^{31}$ represents hydrogen or C$_1$-C$_4$-alkyl, and
R$^{32}$ represents halogen or C$_1$-C$_4$-alkyl.

2. A biphenylcarboxamide of formula (I) as claimed in claim 1 in which
R represents hydrogen, C$_1$-C$_4$-alkyl, or C$_1$-C$_3$-haloalkyl having 1 to 7 fluorine, chlorine, and/or bromine atoms,
Z represents C$_3$-C$_6$-alkenyl or C$_3$-C$_6$-alkynyl; represents C$_3$-C$_6$-haloalkenyl or C$_3$-C$_6$-haloalkynyl having 1 to 5 fluorine, chlorine, and/or bromine atoms; or represents (C$_3$-C$_6$-cycloalkyl)-(C$_1$-C$_4$-alkyl), X and Y independently of one another represent fluorine, chlorine, bromine, cyano, nitro, C$_1$-C$_6$-alkyl, C$_1$-C$_6$-alkoxy, or C$_1$-C$_6$-alkylthio, or represent C$_1$-C$_2$-haloalkyl, C$_1$-C$_2$-haloalkoxy, or C$_1$-C$_2$-haloalkylthio having 1 to 5 fluorine, chlorine, and/or bromine atoms, m represents 0, 1, 2, or 3, with the proviso that X represents identical or different radicals when m represents 2 or 3,
n represents 0, 1, 2, or 3, with the proviso that Y represents identical or different radicals when m represents 2 or 3,
and
A represents
(i) a radical of the formula

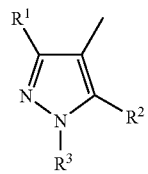

in which
R$^1$ represents hydrogen, cyano, fluorine, chlorine, bromine, iodine, methyl, ethyl, isopropyl, cyclopropyl, methoxy, ethoxy, methylthio, ethylthio, aminocarbonyl, aminocarbonylmethyl, amino-carbonylethyl; represents C$_1$-C$_2$-haloalkyl or C$_1$-C$_2$-haloalkoxy having 1 to 5 fluorine, chlorine, and/or bromine atoms; or represents trifluoromethylthio or difluoromethylthio, R$^2$ represents hydrogen, fluorine, chlorine, bromine, iodine, methyl, ethyl, methoxy, ethoxy, methylthio, or ethylthio, and R$^3$ represents hydrogen, methyl, ethyl, n-propyl, isopropyl, hydroxymethyl, hydroxyethyl, cyclopropyl, cyclopentyl, or cyclohexyl; represents C$_1$-C$_2$-haloalkyl having 1 to 5 fluorine, chlorine, and/or bromine atoms; or represents phenyl, or (ix) a radical of the formula

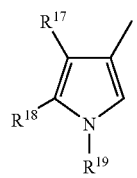

in which
R$^{17}$ represents fluorine, chlorine, bromine, cyano, methyl, ethyl, or isopropyl, or represents C$_1$-C$_2$-haloalkyl having 1 to 5 fluorine, chlorine, and/or bromine atoms, R$^{18}$ represents hydrogen, fluorine, chlorine, bromine, methyl, or ethyl, or represents C$_1$-C$_2$-haloalkyl having 1 to 5 fluorine, chlorine, and/or bromine atoms, and R$^{19}$ represents hydrogen, methyl, or ethyl; represents C$_1$-C$_2$-haloalkyl having 1 to 5 fluorine, chlorine, and/or bromine atoms; or represents C$_1$-C$_2$-alkoxy-C$_1$-C$_2$-alkyl, hydroxymethyl, hydroxylethyl, methylsulfonyl, or dimethylaminosulfonyl, or
(xii) a radical of the formula

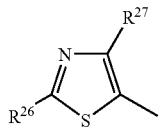

in which
R²⁶ represents hydrogen, fluorine, chlorine, bromine, amino, $C_1$-$C_4$-alkylamino, di($C_1$-$C_4$-alkyl)amino, cyano, methyl, or ethyl, or $C_1$-$C_2$-haloalkyl having 1 to 5 fluorine, chlorine, and/or bromine atoms, and
R²⁷ represents fluorine, chlorine, bromine, methyl, ethyl, or $C_1$-$C_2$-haloalkyl having 1 to 5 fluorine, chlorine, and/or bromine atoms,
or
(xiii) a radical of the formula

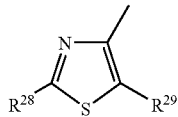

in which
R²⁸ represents hydrogen, fluorine, chlorine, bromine, amino, $C_1$-$C_4$-alkylamino, di($C_1$-$C_4$-alkyl)amino, cyano, methyl, or ethyl, or represents $C_1$-$C_2$-haloalkyl having 1 to 5 fluorine, chlorine, and/or bromine atoms, and
R²⁹ represents fluorine, chlorine, bromine, methyl, or ethyl, or $C_1$-$C_2$-haloalkyl having 1 to 5 fluorine, chlorine, and/or bromine atoms,
or
(xiv) a radical of the formula

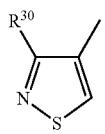

in which R³⁰ represents fluorine, chlorine, bromine, methyl, or ethyl, or $C_1$-$C_2$-haloalkyl having 1 to 5 fluorine, chlorine, and/or bromine atoms,
or
(xv) a radical of the formula

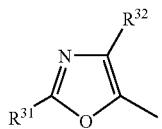

in which
R³¹ represents hydrogen, methyl, or ethyl, and
R³² represents fluorine, chlorine, bromine, methyl, or ethyl.

3. A biphenylcarboxamide of formula (I) as claimed in claim 1 in which

R represents hydrogen, methyl, ethyl, isopropyl, or tert-butyl,
Z represents allyl, 2-butenyl, 2-methylallyl, 1-methylallyl, 3-methyl-2-butenyl, propargyl, 2-butynyl, 3-butynyl, 2-methyl-3-butynyl, 3,3-difluoroallyl, 3,3-dichloroallyl, cyclopropylmethyl, cyclopentylmethyl, or cyclohexylmethyl,
X and Y independently of one another represent fluorine, chlorine, bromine, cyano, nitro, methyl, ethyl, n-propyl, isopropyl, n-butyl, sec-butyl, isobutyl, tert-butyl, methoxy, ethoxy, methylthio, trichloromethyl, trifluoromethyl, difluoromethyl, difluorochloromethyl, difluoromethoxy, trifluoromethoxy, trifluoromethylthio, or difluorochloromethylthio,
m represents 0 or 1,
n represents 0, 1, or 2, with the proviso that Y represents identical or different radicals when n represents 2, and
A represents
(i) a radical of the formula

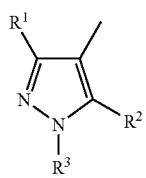

in which
R¹ represents hydrogen, fluorine, chlorine, bromine, iodine, methyl, ethyl, isopropyl, cyclopropyl, methoxy, ethoxy, methylthio, ethylthio, monofluoromethyl, difluoromethyl, trifluoromethyl, difluoro-chloromethyl, trichloromethyl, trifluoromethoxy, trichloromethoxy, trifluoromethylthio, or difluoromethylthio,
R² represents hydrogen, fluorine, chlorine, bromine, iodine, methyl, ethyl, methoxy, ethoxy, methylthio, or ethylthio, and
R³ represents hydrogen, methyl, ethyl, hydroxymethyl, hydroxyethyl, trifluoromethyl, difluoromethyl, or phenyl,
or
(ix) a radical of the formula

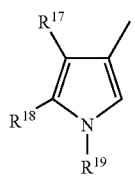

in which
R¹⁷ represents fluorine, chlorine, bromine, cyano, methyl, ethyl, isopropyl, trifluoromethyl, difluoromethyl, difluorochloromethyl, or trichloromethyl,
R¹⁸ represents hydrogen, fluorine, chlorine, bromine, methyl, ethyl, trifluoromethyl, difluoromethyl, or trichloromethyl, and
R¹⁹ represents hydrogen, methyl, ethyl, trifluoromethyl, methoxymethyl, ethoxymethyl, hydroxymethyl, or hydroxyethyl, or
(xii) a radical of the formula

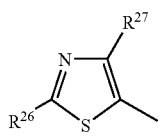

in which
R²⁶ represents hydrogen, fluorine, chlorine, bromine, amino, methylamino, dimethylamino, cyano, methyl, ethyl, trifluoromethyl, difluoromethyl, difluorochloromethyl, or trichloromethyl, and
R²⁷ represents fluorine, chlorine, bromine, methyl, ethyl, trifluoromethyl, difluoromethyl, difluorochloromethyl, or trichloromethyl,
or
(xiii) a radical of the formula

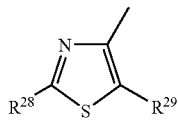

in which
R²⁸ represents hydrogen, fluorine, chlorine, bromine, amino, methylamino, dimethylamino, cyano, methyl, ethyl, trifluoromethyl, difluoromethyl, difluorochloromethyl, or trichloromethyl, and
R²⁹ represents fluorine, chlorine, bromine, methyl, ethyl, trifluoromethyl, difluoromethyl, difluorochloromethyl, or trichloromethyl,
or
(xiv) a radical of the formula

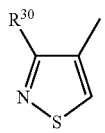

in which R³⁰ represents fluorine, chlorine, bromine, methyl, ethyl, trifluoromethyl, difluoromethyl, difluorochloromethyl, or trichloromethyl, or
(xv) a radical of the formula

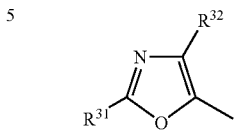

in which
R³¹ represents hydrogen, methyl, or ethyl, and
R³² represents fluorine, chlorine, bromine, methyl, or ethyl, including a stereoisomer thereof, or a pharmaceutically acceptable salt thereof.

4. A biphenylcarboxamide as claimed in claim 1 having formula (I-1)

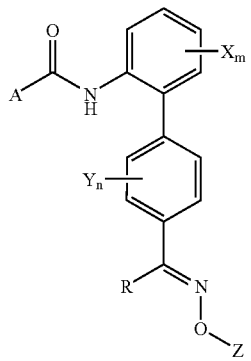

(I-1)

in which R, Z, X, Y, m, n, and A are as defined for formula (I) in claim 1.

5. A composition for controlling unwanted microorganisms comprising one or more biphenylcarboxamides of formula (I) as claimed in claim 1 and one or more extenders and/or surfactants.

6. A method for controlling unwanted microorganisms comprising applying an effective amount of one or more biphenylcarboxamides of formula (I) as claimed in claim 1 to the microorganisms and/or their habitat.

* * * * *